(12) United States Patent
Picard et al.

(10) Patent No.: US 6,828,326 B2
(45) Date of Patent: Dec. 7, 2004

(54) PYRIMIDINONE FUSED BICYCLIC METALLOPROTEINASE INHIBITORS

(75) Inventors: Joseph Armand Picard, Canton, MI (US); Michael William Wilson, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/634,225

(22) Filed: Aug. 5, 2003

(65) Prior Publication Data
US 2004/0043991 A1 Mar. 4, 2004

Related U.S. Application Data
(60) Provisional application No. 60/403,149, filed on Aug. 13, 2002.

(51) Int. Cl.$^7$ .................... C07D 513/04; A61K 31/433
(52) U.S. Cl. ................. 514/259.1; 514/259.2; 514/259.3; 514/259.31; 514/259.5; 544/263; 544/255; 544/278; 544/281; 544/282
(58) Field of Search .................... 544/263, 255, 544/278, 281, 282; 514/259.1, 259.2, 259.3, 259.31, 259.5

(56) References Cited

U.S. PATENT DOCUMENTS

| | | | |
|---|---|---|---|
| 3,810,894 A | * | 5/1974 | Kranz et al. ............... 544/247 |
| 6,008,243 A | | 12/1999 | Bender et al. |
| 6,656,932 B2 | | 12/2003 | Picard et al. |
| 2002/0151555 A1 | | 10/2002 | Barvian et al. |
| 2002/0151558 A1 | | 10/2002 | Andrianjara et al. |
| 2002/0156061 A1 | | 10/2002 | Barvian et al. |
| 2002/0156069 A1 | | 10/2002 | Picard et al. |
| 2002/0161000 A1 | | 10/2002 | Barvian et al. |
| 2002/0193377 A1 | | 12/2002 | Andrianjara et al. |
| 2003/0004172 A1 | | 1/2003 | Harter et al. |
| 2003/0078276 A1 | | 4/2003 | Andrianjara et al. |
| 2003/0087924 A1 | | 5/2003 | Sorenson |
| 2003/0130278 A1 | | 7/2003 | Gaudilliere et al. |
| 2003/0144274 A1 | | 7/2003 | Bunker et al. |
| 2003/0216402 A1 | | 11/2003 | Gaudilliere et al. |
| 2003/0220355 A1 | | 11/2003 | Gaudilliere et al. |
| 2004/0006077 A1 | | 1/2004 | Gaudilliere et al. |

FOREIGN PATENT DOCUMENTS

| | | |
|---|---|---|
| EP | 0 935 963 A2 A3 | 8/1999 |
| EP | 1 138 680 A1 | 10/2001 |
| JP | 57-142989 | 9/1982 |
| WO | WO 00/09485 A1 | 2/2000 |
| WO | WO 01/12611 A1 | 2/2001 |
| WO | WO 01/49700 A1 | 7/2001 |
| WO | WO 01/63244 A1 | 8/2001 |
| WO | WO 02/34726 A2 A3 | 5/2002 |
| WO | WO 02/34753 A2 A3 | 5/2002 |
| WO | WO 02/064568 A1 | 8/2002 |
| WO | WO 02/064571 A1 | 8/2002 |
| WO | WO 02/064572 A1 | 8/2002 |
| WO | WO 02/064578 A1 | 8/2002 |
| WO | WO 02/064595 A1 | 8/2002 |
| WO | WO 02/064598 A1 | 8/2002 |
| WO | WO 02/064599 A1 | 8/2002 |
| WO | WO 02/064080 A2 A3 | 8/2002 |
| WO | WO 02/064547 A2 A3 | 8/2002 |
| WO | WO 03/032999 A1 | 4/2003 |
| WO | WO 03/033478 A1 | 4/2003 |
| WO | WO 03/076417 A2 A3 | 9/2003 |
| WO | WO 04/000322 A1 | 12/2003 |

OTHER PUBLICATIONS

Nagamatsu et al., The first reliable, General synthesis of the 5–oxo derivatives of 5,6–dihydro–1,2,4–triazolo[4,3–c]pyrimidine and the rates of isomerization of the [4,3–c] compounds into their [1,5–c] isomers, Heterocycles, 57(4):631–636, Apr. 2002.*
Hayakawa et a., CAPLUS Abstract 133:4331, 2000.*
Zvezdina et al., CAPLUS Abstract 107:198225, 1987.*
Ivanov et al., CAPLUS Abstract 100:68258, 1984.*
Kost et al., CAPLUS Abstract 90:72145, 1979.*
Simone, Oncology: Introduction, Cecil Textbook of Medicine, 20$^{th}$ Edition, vol. 2, pp. 1004–1010, 1996.*
Layzer, Degenerative Diseases of the Nervous System, Cecil Textbook of Medicine, 2050–7, 1996.*
Damasio, Alzheimer's Disease and Related Dementias, Cecil Textbook of Medicine, 1992–6, 1996.*
Morris et al., PubMed Abstract (Invasion Metastasis 17(6):281–96), 1997.*
Rasmussen et al., Martix Metalloproteinase Inhibition as a Novel Anticancer Strategy, Pharmacol. Ther., vol. 75, No. 1, pp. 69–75, 1997.*
Chambers et al., Changing Views of the Role of Matrix Metalloproteinases in Metastasis, J. National Cancer Institute, vol. 89, No. 17, pp. 1260–1270, 1997.*
Billinghurst, et al., Comparison of the Degradation of Type II Collagen and Proteoglycan in Nasal and Articular Cartilages Induced by Interleukin–1 and the Selective Inhibition of Type II Collagen Cleavage by Collagenase, Arthritis & Rheumatism, 2000; 43(3): 664–672.
Billinghurst, et al., Enhanced Cleavage of Type II Collagen by Collagenases in Osteoarthritic Articular Cartilage, J. Clin Invest., 1997; 99(7): 1534–1545.
Chen, et al., Structure–Based Design of a Novel, Potent, and selective Inhibitor for MMP–13 Utilizing NMR Spectroscopy and Computer–Aided Molecular Design, J. Am. Chem. Soc., 2000; 122: 9648–9654.

(List continued on next page.)

*Primary Examiner*—Deepak Rao
(74) *Attorney, Agent, or Firm*—Pfizer Inc.; Pamela C. Ancona; Claude F. Purchase, Jr.

(57) ABSTRACT

The present invention relates to fused bicyclic metalloproteinase inhibitors of the formula

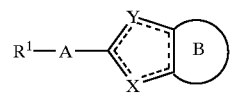

wherein A, B, X, Y, and $R^1$ are as defined in the specification, and to pharmaceutical compositions and methods of treating arthritis, inflammation, cancer and other disorders.

9 Claims, No Drawings

OTHER PUBLICATIONS

Dahlberg, et al., Selective Enhancement of Collagenase–mediated Cleavage of Resident Type II Collagen in Cultured Osteroarthritic Cartilage and Arrest with a Synthetic Inhibitor that Spares Collagenase 1 (Matrix Metalloproteinase2), Arthritis & Rheumatism, 2000; 43(3): 673–682.

Hirota, et al., Novel Synthesis of Pyrido[3,4–d]pyrimidines, Pyrido[2,3–d]pyrimidines, and Quinazolines via Palladium–catalyzed Oxidative Coupling, Heterocycles, 1994; 37(1): 563–570.

Lovejoy, et al., Crystal structures of MMP–1 AND –13 reveal the structural basis for selectivity of collagenase inhibitors, Nature Structural Biology, 1999; 6(3): 217–221.

Mitchell, et al., Cloning, Expression, and Type II Collagenolytic Activity of Matrix Metaloproteinase–13 from Human Osteoarthritic, Cartilage, J. Clin. Invest., 1996; 97: 761–768.

Moy, et al., High–resolution Solution Structure of the Cataliytic Fragment of Human Collagenase–3 (MMP–3) Complexed with a Hydroxamic Acid Inhibitor, J. Mol. Biol., 2000; 302: 671–689.

Natchus, et al., Development of New Carboxylic Acid–Based MMP Inhibitors Derived from Functionalized Propargylglycines, J. Med. Chem., 2001; 44: 1060–1071.

Neuhold, et al., Postnatal expression in hyaline cartilage of constitutively active human collagenase–3 (MMP–13) induces osteoarthritis in mice, J. CLin. Invest., 2001; 107(1): 35–44.

Wamhoff, et al., An Efficient Synthesis of Thioisom Unchnones Derived from Uracils and Uridine: A Novel Type of Mesonionic Necleosides, Organic Letters, 2000; 2(5): 581–584.

Patent Abstracts of Japan vol. 006, no 244(C138); 1982 Pub. No. 57142989.

U.S. patent application Ser. No. 10/071,032, Dyer et al., filed Feb. 8, 2002.

U.S. patent application Ser. No. 10/634,531, Johnson, filed Aug. 5, 2003.

U.S. patent application Ser. No. 10/634,709, Bunker et al., filed Aug. 5, 2003.

U.S. patent application Ser. No. 10/634,162, Wilson, filed Aug. 5, 2003.

U.S. patent application Ser. No. 10/634,473, Bunker et al., filed Aug. 5, 2003.

U.S. patent application Ser. No. 10/634,289, Bunker et al., filed Aug. 5, 2003.

U.S. patent application Ser. No. 10/634,180, Bunker et al., filed Aug. 5, 2003.

U.S. patent application Ser. No. 10/634,712, Hicks et al., filed Aug. 5, 2003.

U.S. patent application Ser. No. 10/634,181, Li, filed Aug. 5, 2003.

U.S. patent application Ser. No. 10/634,489, Roark, filed Aug. 5, 2003.

U.S. patent application Ser. No. 10/634,420, Roark, filed Aug. 5, 2003.

U.S. patent application Ser. No. 10/634,716, Nahra et al., filed Aug. 5, 2003.

U.S. patent application Ser. No. 10/634,288, O'Brien, filed Aug. 5, 2003.

U.S. patent application Ser. No. 10/634,717, Nahra et al., filed Aug. 5, 2003.

U.S. patent application Ser. No. 10/634,177, Wilson, filed Aug. 5, 2003.

U.S. patent application Ser. No. 10/634,290, Wilson, filed Aug. 5, 2003.

U.S. patent application Ser. No. 10/634,182, Li, filed Aug. 5, 2003.

U.S. patent application Ser. No. 10/634,419, Hicks et al., filed Aug. 5, 2003.

U.S. patent application Ser. No. 10/634,713, Picard, filed Aug. 5, 2003.

U.S. patent application Ser. No. 10/634,718, Ortwine, filed Aug. 5, 2003.

U.S. patent application Ser. No. 10/739,261, Bunker et al., filed Dec. 18, 2003.

* cited by examiner

PYRIMIDINONE FUSED BICYCLIC METALLOPROTEINASE INHIBITORS

CROSS-REFERENCE TO RELATED APPLICATIONS

This application claims benefit of priority from U.S. Provisional Patent Application No. 60/403,149, filed Aug. 13, 2002.

BACKGROUND OF THE INVENTION

The present invention relates to fused bicyclic metalloproteinase inhibitors, and to pharmaceutical compositions and methods of treatment of inflammation, cancer and other disorders.

The compounds of the present invention are inhibitors of zinc metalloendopeptidases, especially those belonging to the class of matrix metalloproteinases (also called MMP or matrixin). Matrix metalloproteinases (sometimes referred to as MMPs) are naturally occurring enzymes found in most mammals. Over-expression and activation of MMPs, or an imbalance between MMPs and inhibitors of MMPs, may besuggested as factors in the pathogenesis of diseases characterized by the breakdown of extracellular matrix or connective tissues.

Stromelysin-1 and gelatinase A are members of the MMP family. Other members include fibroblast collagenase (MMP-1), neutrophil collagenase (MMP-8), gelatinase B (92 kDa gelatinase) (MMP-9), stromelysin-2 (MMP-10), stromelysin-3 (MMP-11), matrilysin (MMP-7), collagenase 3 (MMP-13), TNF-alpha converting enzyme (TACE), and other newly discovered membrane-associated matrix metalloproteinases (Sato H., Takino T., Okada Y., Cao J., Shinagawa A., Yamamoto E., and Seiki M., Nature, 1994;370:61–65). In total, the MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., J. Clin. Invest., 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

These enzymes may beimplicated with a number of diseases which result from breakdown of connective tissue, including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these and other diseases is now recognized to be by inhibiting matrix metalloproteinase enzymes, thereby curtailing and/or eliminating the breakdown of connective tissues that results in the disease states. It has also been recognized that different combinations of MMP's are expressed in different pathological situations. As such, inhibitors with specific selectivities for individual MMP's may be preferred for individual diseases.

There is a catalytic zinc domain in matrix metalloproteinases that is typically the focal point for inhibitor design. The modification of substrates by introducing zinc-chelating groups has generated potent inhibitors such as peptide hydroxamates and thiol-containing peptides. Peptide hydroxamates and the natural endogenous inhibitors of MMPs (TIMPS) may beused successfully to treat animal models of cancer and inflammation. MMP inhibitors have also been used to prevent and treat congestive heart failure and other cardiovascular diseases, U.S. Pat. No. 5,948,780.

A major limitation on the use of currently known MMP inhibitors is their lack of specificity for any particular enzyme. Recent data has established that specific MMP enzymes are associated with some diseases, with no effect on others. The MMPs are generally categorized based on their substrate specificity, and indeed the collagenase subfamily of MMP-1, MMP-8, and MMP-13 selectively cleave native interstitial collagens, and thus are associated only with diseases linked to such interstitial collagen tissue. This is evidenced by the recent discovery that MMP-13 alone is over expressed in breast carcinoma, while MMP-1 alone is over expressed in papillary carcinoma (see Chen et al., J. Am. Chem. Soc., 2000;122:9648–9654).

There appears to be few selective inhibitors of MMP-13 reported. A compound named WAY-170523 has been reported by Chen et al., supra., 2000, and a few other compounds are reported in PCT International Application Publication Number WO 01/63244 A1, as allegedly selective inhibitors of MMP-13. Further, U.S. Pat. No. 6,008,243 discloses inhibitors of MMP-13. However, no selective or nonselective inhibitor of MMP-13 has been approved and marketed for the treatment of any disease in any mammal. Accordingly, the need continues to find new low molecular weight compounds that are potent and selective MMP inhibitors, and that have an acceptable therapeutic index of toxicity/potency to make them amenable for use clinically in the prevention and treatment of the associated disease states. An object of this invention is to provide a group of selective MMP-13 inhibitor compounds characterized as fused bicyclics.

Matrix metalloproteinase inhibitors are well known in the literature. Hydroxamic acid MMP inhibitors are exemplified in European Patent Publication 606,046, published Jul. 13, 1994. Several pyrimidine-2,4,6 trione MMP inhibitors are referred to in PCT publication WO 98/58925, published Dec. 30, 1998. PCT publication WO 00/47565, published Aug. 17, 2000 refers to certain aryl substituted fused bicyclic MMP inhibitors. U.S. Non-provisional application Ser. No. 09/635,156, filed Aug. 9, 2000 (which claims priority to U.S. Provisional application No. 60/148,547 filed Aug. 12, 1999) refers to heteroaryl substituted pyrimidine-2,4,6 trione MMP inhibitors. United States Provisional Application entitled "Spiro-Fused bicyclic Metalloproteinase Inhibitors", filed Oct. 26, 2000, refers to certain 5-spiro pyrimidin-2,4,6-triones. Barbituric acids and methods for their preparation are well known in the art, see for example Goodman and Gilman's, "The Phamacological Basis of Therapeutics," 345–382 (Eighth Edition, McGraw Hill, 1990). Each of the above referenced publications and applications is hereby incorporated by reference in its entirety

SUMMARY OF THE INVENTION

The present invention relates to compounds of the formula:

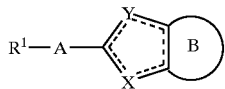

(I)

wherein A is a suitable linker such as

—NR(C=O)—,
—(C=O)NR,
$(C_2-C_6)$alkynyl-,
a bond,
—OC(O)—;
—CH(R)C(O)—;
—OC(NR)—;
—CH(R)C(NR)—;
—N(R)C(O)—;
—N(R)C(S)—;
—N(R)C(NR)—;
—SC(O)—;
—CH(R)C(S)—;
—SC(NR)—;
—C≡CCR$_2$—;
—OCH$_2$—;
—N(R)CH$_2$—;
—C≡C—;
—CR$_2$C≡C—;
—CF$_2$C≡C—;
—C≡CCF$_2$—;

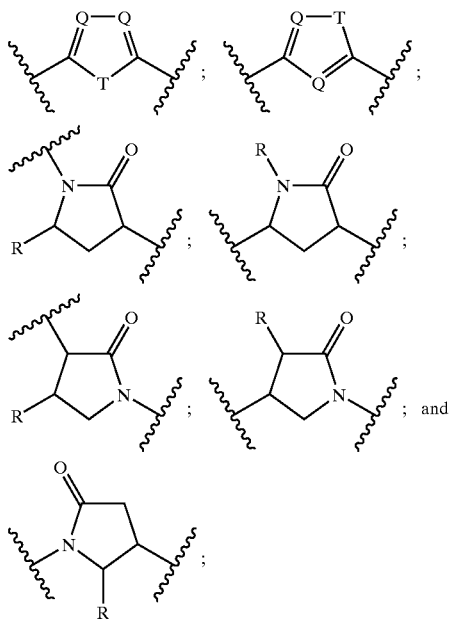

Q is independently C(H) or N; and
T is O, S, N(H), or N($C_1-C_6$ alkyl);
and pharmaceutically acceptable salts thereof;

X is selected from —N=, —NR$^9$—, —O—, —S—, —CR$^{10}$, >C(R$^{11}$)$_2$,

Y is selected from —N=, —NR$^9$—, —O—, —S—, —CR$^{10}$—, >C(R$^{11}$)$_2$;

with the proviso that when Y is O or S, X is not O or S;

dashed lines represent optional double bonds;

R, R$^1$, R$^9$, R$^{10}$, and R$^{11}$ are the same or different where ever they appear and each is independently selected from the group consisting of hydrogen, $(C_1-C_6)$alkyl-, $(C_2-C_6)$alkenyl-, $(C_2-C_6)$alkynyl-, $(C_3-C_{10})$cycloalkyl-, $(C_6-C_{10})$aryl-, $(C_1-C_{10})$heterocyclyl-, $((C_1-C_{10})$heteroaryl-, $(C_3-C_{10})$cycloalkyl-$(C_1-C_6)$alkyl-, $(C_6-C_{10})$aryl-$(C_1-C_6)$alkyl-, $(C_1-C_{10})$heterocyclyl-$(C_1-C_6)$alkyl-, $(C_1-C_{10})$heteroaryl-$(C_1-C_6)$alkyl-, $(C_3-C_{10})$cycloalkyl-$(C_2-C_6)$alkenyl-, $(C_6-C_{10})$aryl-$(C_2-C_6)$alkenyl-, $(C_1-C_{10})$heterocyclyl-$(C_2-C_6)$alkenyl-, $(C_6-C_{10})$aryl-$(C_2-C_6)$alkenyl-, $(C_1-C_{10})$heteroaryl-$(C_2-C_6)$alkenyl-, $(C_3-C_{10})$cycloalkyl-$(C_2-C_6)$alkynyl-, $(C_6-C_{10})$aryl-$(C_2-C_6)$alkynyl-, $(C_1-C_{10})$ heterocyclyl-$(C_2-C_6)$alkynyl-, and $(C_1-C_{10})$heteroaryl-$(C_2-C_6)$alkynyl-; wherein each of the aforesaid group members, $(C_1-C_6)$alkyl-, $(C_2-C_6)$alkenyl-, $(C_2-C_6)$alkynyl-, $(C_3-C_{10})$cycloalkl-, $(C_6-C_{10})$aryl-, $(C_1-C_{10})$heterocyclyl-, $(C_1-C_{10})$heteroaryl-, $(C_3-C_{10})$cycloalkyl-$(C_1-C_6)$alkyl-, $(C_6-C_{10})$aryl-$(C_1-C_6)$alkyl-, $(C_1-C_{10})$heterocyclyl-$(C_1-C_6)$alkyl-, $(C_1-C_{10})$heteroaryl$(C_1-C_6)$alkyl-, $(C_3-C_{10})$cycloalkyl-$(C_2-C_6)$alkenyl-, $(C_6-C_{10})$aryl-$(C_2-C_6)$alkenyl-, $(C_1-C_{10})$heterocyclyl-$(C_2-C_6)$alkenyl-, $(C_6-C_{10})$aryl-$(C_2-C_6)$alkenyl-, $(C_1-C_{10})$heteroaryl-$(C_2-C_6)$alkenyl-, $(C_3-C_{10})$cycloalkyl-$(C_2-C_6)$alkynyl-, $(C_6-C_{10})$aryl-$(C_2-C_6)$alkynyl-, $(C_1-C_{10})$heterocyclyl-$(C_2-C_6)$alkynyl-, and $(C_1-C_{10})$heteroaryl-$(C_2-C_6)$alkynyl-, may be optionally independently substituted with one to three suitable substituents selected from the group consisting of hydrogen, halogen, hydroxy, —CN, $(C_1-C_4)$alkyl-, $(C_1-C_4)$alkoxy-, CF$_3$—, CF$_3$O—, $(C_6-C_{10})$aryl-, $(C_1-C_{10})$heteroaryl-, $(C_6-C_{10})$aryl-$(C_1-C_4)$alkyl-, $(C_1-C_{10})$heteroaryl-$(C_1-C_4)$alkyl-, HO(C=O)—, $(C_1-C_4)$alkyl -(O)(C=O)—, $(C_1-C_4)$alkyl- (O)(C=O) $(C_1-C_4)$alkyl-,$(C_1-C_4)$alkyl-(C=O)$(C_1-C_4)$alkyl-, —(S=O)R, —(SO$_2$)R, and NR$^7$R$^8$ wherein R$^7$ and R$^8$ are independently selected from hydrogen and $(C_1-C_6)$ alkyl;

ring B is selected from the group consisting of:

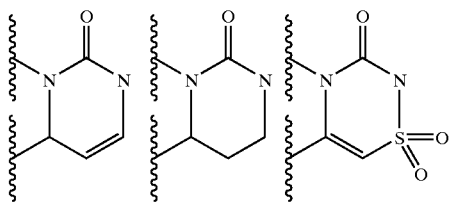

wherein the X, Y, B ring may be optionally substituted with one to three suitable substituents.

and pharmaceutically acceptable salts thereof.

The present invention also provides a compound of the formula (I):

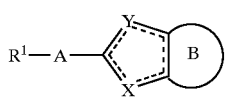
(I)

wherein A is —NR(C=O), —(C=O)NR, (C$_2$-C$_6$) alkynyl-, or a bond;

X is selected from —N=, —NR$^9$—, —O—, —S—, —CR$^{10}$—, >C(R$^{11}$)$_2$,

Y is selected from —N=, —NR$^9$—, —O—, —S—, —CR$^{10}$—, >C(R$^{11}$)$_2$;

with the proviso that when Y is O or S, X is not O or S;

dashed lines represent optional double bonds;

ring B is selected from the group consisting of:

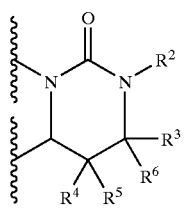

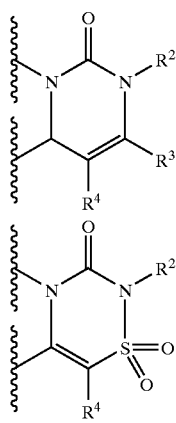

wherein each R, R$^1$, R$^2$, R$^3$, R$^5$, R$^6$, R$^9$, R$^{10}$, and R$^{11}$ are the same or different, where ever they appear, and each is independently selected from the group consisting of hydrogen, (C$_1$-C$_6$)alkyl-, (C$_2$-C$_6$)alkenyl-, (C$_2$-C$_6$) alkynyl-, (C$_3$-C$_{10}$)cycloalkyl-, (C$_6$-C$_{10}$)aryl-, (C$_1$-C$_{10}$)heterocyclyl-,(C$_1$-C$_{10}$)heteroaryl-, (C$_3$-C$_{10}$) cycloalkyl-(C$_1$-C$_6$)alkyl-, (C$_6$-C$_{10}$)aryl-(C$_1$-C$_6$)alkyl-, (C$_1$-C$_{10}$)heterocyclyl-(C$_1$-C$_6$)alkyl-, (C$_1$-C$_{10}$) heteroaryl-(C$_1$-C$_6$)alkyl-, (C$_3$-C$_{10}$)cycloalkyl-(C$_2$-C$_6$) alkenyl-, (C$_6$-C$_{10}$)aryl-(C$_2$-C$_6$)alkenyl-, (C$_1$-C$_{10}$) heterocyclyl-(C$_2$-C$_6$)alkenyl-, (C$_6$-C$_{10}$)aryl-(C$_2$-C$_6$) alkenyl-, (C$_1$-C$_{10}$)heteroaryl-(C$_2$-C$_6$)alkenyl-, C$_1$-C$_6$) alkynyl-, (C$_6$-C$_{10}$)aryl-(C$_2$-C$_6$)alkynyl-, (C$_1$-C$_{10}$) heterocyclyl-(C$_2$-C$_6$)alkynyl-, (C$_1$-C$_{10}$)heteroaryl-(C$_2$-C$_6$)alkynyl-; wherein each of the aforesaid group members, (C$_1$-C$_6$)alkyl-, (C$_2$-C$_6$)alkenyl-, (C$_2$-C$_6$) alkynyl-, (C$_3$-C$_{10}$)cycloalkyl-, (C$_6$-C$_{10}$)aryl-, (C$_1$-C$_{10}$)heterocyclyl-, (C$_1$-C$_{10}$)heteroaryl-, (C$_3$-C$_{10}$) cycloalkyl-(C$_1$-C$_6$)alkyl-, (C$_6$-C$_{10}$)aryl-(C$_1$-C$_6$)alkyl-, (C$_1$-C$_{10}$)heterocyclyl-(C$_1$-C$_6$)alkyl-, (C$_1$-C$_{10}$) heteroaryl-(C$_1$-C$_6$)alkyl-, (C$_3$-C$_{10}$)cycloalkyl-(C$_2$-C$_6$) alkenyl-, (C$_6$-C$_{10}$)aryl-(C$_2$-C$_6$)alkenyl-, (C$_1$-C$_{10}$) heterocyclyl-(C$_2$-C$_6$)alkenyl-, (C$_6$-C$_{10}$)aryl-(C$_2$-C$_6$) alkenyl-, (C$_1$-C$_{10}$)heteroaryl-(C$_2$-C$_6$)alkenyl-, (C$_3$-C$_{10}$)cycloalkyl-(C$_2$-C$_6$)alkynyl-, (C$_6$-C$_{10}$)aryl-(C$_2$-C$_6$)alkynyl-, (C$_1$-C$_{10}$)heterocyclyl-(C$_2$-C$_6$) alkynyl-, and (C$_1$-C$_{10}$)heteroaryl-(C$_2$-C$_6$)alkynyl-, may be optionally independently substituted with one to three suitable substituents selected from the group consisting of hydrogen, halogen, hydroxy, —CN, (C$_1$-C$_4$)alkyl-, (C$_1$-C$_4$)alkoxy-, CF$_3$—, CF$_3$O—, (C$_6$-C$_{10}$)aryl-, (C$_1$-C$_{10}$)heteroaryl-, (C$_6$-C$_{10}$)aryl-C$_1$-C$_4$)alkyl-, (C$_1$-C$_{10}$)heteroaryl-(C$_1$-C$_4$)alkyl-, HO(C=O)—, (C$_1$-C$_4$)alkyl-(O)(C=O)—, (C$_1$-C$_4$) alkyl-(O)(C=O)(C$_1$-C$_4$)alkyl-, (C$_1$-C$_4$)alkyl-(C=O)—, (C$_1$-C$_4$)alkyl-(C=O)(C$_1$-C$_4$)alkyl-, —(S=O)R, —(SO$_2$)R, and NR$^7$R$^8$ wherein R$^7$ and R$^8$ are independently selected from hydrogen, (C$_1$-C$_6$) alkyl;

R$^4$ is selected from the group consisting of hydrogen and (C$_1$-C$_6$)alkyl-, and R$^4$ may be optionally substituted with one to three suitable substituents selected from the group consisting of halogen, hydroxy, —CN, CF$_3$—, and CF$_3$O—;

m is an integer from 0–3; and and pharmaceutically acceptable salts thereof.

Thus, the invention provides a compound as defined above which is a fused pyrimidinone of the general formula:

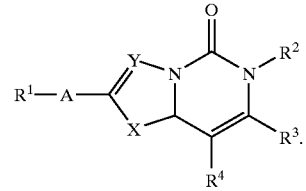

Another embodiment of the invention includes fused pyrimidinone selected from the group consisting of:

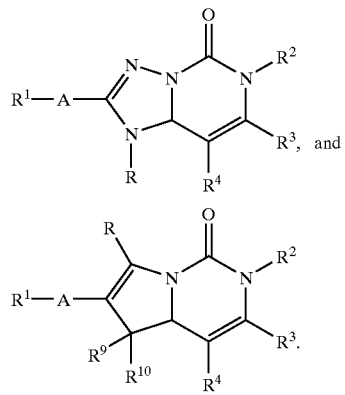

The invention also provides a fused pyrimidinone of the formula:

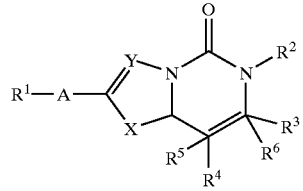

such as fused 2-pyrimidinones selected from the group consisting of:
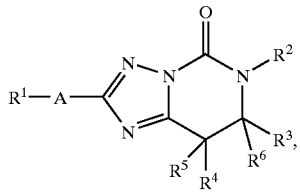
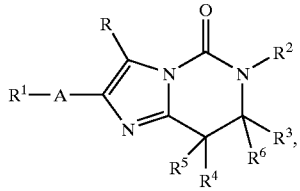
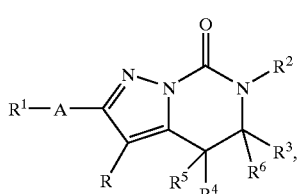
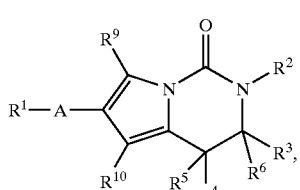
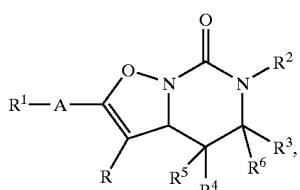
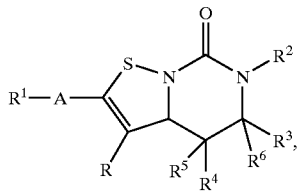
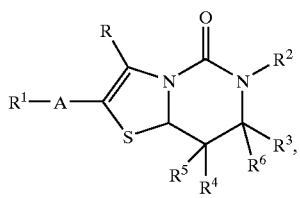
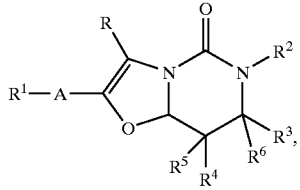
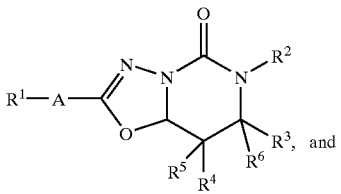
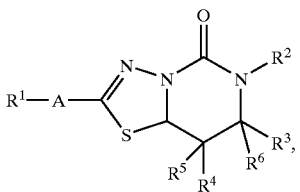
Another embodiment of the invention is a fused sulfone substituted pyrimidinone of the formula:
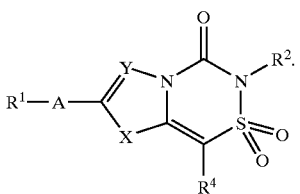
such as fused 4-pyridinones selected from the group consisting of:
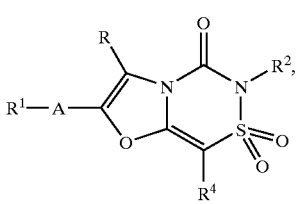
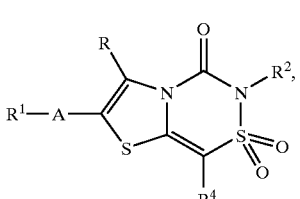
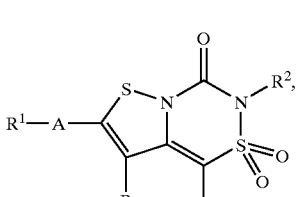
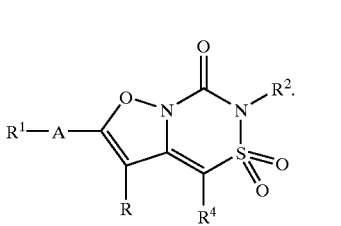

The present invention provides a compound of the formula (I):

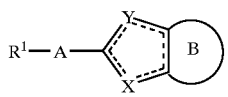

wherein A is —NR(C=O), —(C=O)NR, ($C_2$–$C_6$) alkynyl-, or a bond;
X is selected from —N=, —$NR^9$—, —O—, —S—, —$CR^{10}$—, >$C(R^{11})_2$,
Y is selected from —N=, —$NR^9$—, —O—, —S—, —$CR^{10}$—, >$C(R^{11})_2$;
with the proviso that when Y is O or S, X is not O or S;
dashed lines represent optional double bonds;
ring B is selected from the group consisting of:

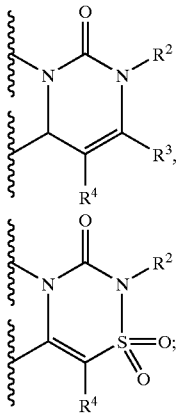

wherein each R, $R^1$, $R^2$, $R^3$, $R^5$, $R^6$, $R^9$, $R^{10}$, and $R^{11}$ are the same or different, where ever they appear, and each is independently selected from the group consisting of ($C_1$–$C_6$)alkyl-, ($C_2$–$C_6$)alkenyl-, ($C_2$–$C_6$)alkynyl-, ($C_3$–$C_{10}$)cycloalkyl-, ($C_6$–$C_{10}$)aryl-$C_1$–$C_{10}$) heterocyclyl-, ($C_1$–$C_{10}$)heteroaryl-, ($C_3$–$C_{10}$) cycloalkyl-($C_1$–$C_6$)alkyl-, ($C_6$–$C_{10}$)aryl-($C_1$–$C_6$)alkyl-, ($C_1$–$C_{10}$)heterocyclyl-($C_1$–$C_6$)alkyl-, ($C_1$–$C_{10}$) heteroaryl-($C_1$–$C_6$)alkyl-, ($C_3$–$C_{10}$)cycloalkyl-($C_2$–$C_6$) alkenyl-, ($C_6$–$C_{10}$)aryl-($C_2$–$C_6$)alkenyl-, ($C_1$–$C_{10}$) heterocyclyl-($C_2$–$C_6$)alkenyl-, ($C_6$–$C_{10}$)aryl-($C_2$–$C_6$) alkenyl-, ($C_1$–$C_{10}$)heteroaryl-($C_2$–$C_6$)alkenyl-, ($C_3$–$C_{10}$)cycloalkyl-($C_2$–$C_6$)alkynyl-, ($C_6$–$C_{10}$)aryl-($C_2$–$C_6$)alkynyl-, ($C_1$–$C_{10}$)heterocyclyl-($C_2$–$C_6$) alkynyl-, ($C_1$–$C_{10}$)heteroaryl-($C_2$–$C_6$)alkynyl-;
wherein each of the aforesaid group members, ($C_1$–$C_6$) alkyl-, ($C_2$–$C_6$)alkenyl-, ($C_2$–$C_6$)alkynyl-, ($C_3$–$C_{10}$) cycloalkyl-, ($C_6$–$C_{10}$)aryl-, ($C_1$–$C_{10}$)heteroaryl-($C_1$–$C_{10}$)heteroaryl-, ($C_3$–$C_{10}$)cycloalkyl-($C_1$–$C_6$) alkyl-, ($C_6$–$C_{10}$)aryl-($C_1$–$C_6$)alkyl-, ($C_1$–$C_{10}$) heterocyclyl-($C_1$–$C_6$)alkyl-, ($C_1$–$C_{10}$)heteroaryl-($C_1$–$C_6$)alkyl-, ($C_3$–$C_{10}$)cycloalkyl-($C_2$–$C_6$)alkenyl-, ($C_6$–$C_{10}$)aryl-($C_2$–$C_6$)alkenyl-, ($C_1$–$C_{10}$)heterocyclyl-($C_2$–$C_6$)alkenyl-, ($C_6$–$C_{10}$)aryl-($C_2$–$C_6$)alkenyl-, ($C_1$–$C_{10}$)heteroaryl-($C_2$–$C_6$)alkenyl-, ($C_3$–$C_{10}$) cycloalkyl-($C_2$–$C_6$)alkynyl-, ($C_6$–$C_{10}$)aryl-($C_2$–$C_6$) alkynyl-, ($C_1$–$C_{10}$)heterocyclyl-($C_2$–$C_6$)alkynyl-, and ($C_1$–$C_{10}$)heteroaryl-($C_2$–$C_6$)alkynyl-, may be optionally independently substituted with one to three suitable substituents selected from the group consisting of hydrogen, halogen, hydroxy, —CN, ($C_1$–$C_4$)alkyl-, ($C_1$–$C_4$)alkoxy-, $CF_3$—, $CF_3O$—, ($C_6$–$C_{10}$)aryl-, ($C_1$–$C_{10}$)heteroaryl-, ($C_6$–$C_{10}$)aryl-($C_1$–$C_4$)alkyl-, ($C_1$–$C_{10}$)heteroaryl-($C_1$–$C_4$)alkyl-, HO(C=O)—, ($C_1$–$C_4$)alkyl-(O)(C=O)—, ($C_1$–$C_4$)alkyl-(O)(C=O) ($C_1$–$C_4$)alkyl-, ($C_1$–$C_4$)alkyl-(C=O)($C_1$–$C_4$)alkyl-, —(S=O)R, —($SO_2$)R, and $NR^7R^8$ wherein $R^7$ and $R^8$ are independently selected from hydrogen, ($C_1$–$C_6$) alkyl;
R, $R^3$, $R^5$, $R^6$, $R^9$, $R^{10}$, and $R^{11}$ may further be hydrogen;
$R^4$ is selected from the group consisting of hydrogen and ($C_1$–$C_6$)alkyl-, and $R^4$ may be optionally substituted with one to three suitable substituents selected from the group consisting of halogen, hydroxy, —CN, $CF_3$—, and $CF_3O$—;
m is an integer from 0–3; or
a pharmaceutically acceptable salt thereof.

The present invention provides a compound of the formula:

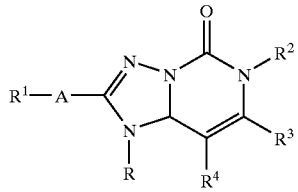

wherein A, R and $R^1$–$R^{11}$ are as defined above.

The present invention also provides a compound of the formula:

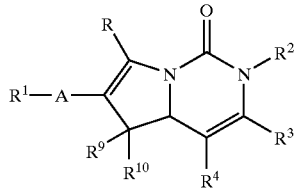

wherein A, R and $R^1$–$R^{11}$ are as defined above.

The present invention also provides a compound of the formula:

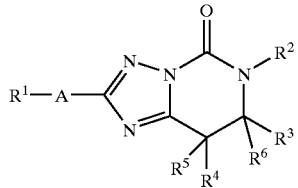

wherein A, R and $R^1$–$R^{11}$ are as defined above.

The present invention also provides a compound of the formula:

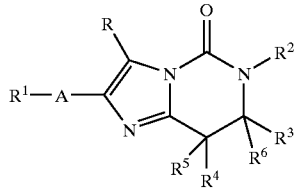

wherein A, R and $R^1$–$R^{11}$ are as defined above.

The present invention also provides a compound of the formula:

[Structure: pyrazolo-fused ring with R¹-A, R, R², R³, R⁴, R⁵, R⁶ substituents, C=O]

wherein A, R and R¹–R¹¹ are as defined above.

The present invention also provides a compound of the formula:

[Structure: pyrrolo-fused ring with R¹-A, R⁹, R¹⁰, R², R³, R⁴, R⁵, R⁶ substituents, C=O]

wherein A, R and R¹–R¹¹ are as defined above.

The present invention also provides a compound of the formula:

[Structure: isoxazolo-fused ring with R¹-A, R, R², R³, R⁴, R⁵, R⁶ substituents, O, C=O]

wherein A, R and R¹–R¹¹ are as defined above.

The present invention also provides a compound of the formula:

[Structure: isothiazolo-fused ring with R¹-A, R, R², R³, R⁴, R⁵, R⁶ substituents, S, C=O]

wherein A, R and R¹–R¹¹ are as defined above.

The present invention also provides a compound of the formula:

[Structure: thiazolo-fused ring with R¹-A, R, R², R³, R⁴, R⁵, R⁶ substituents, S, C=O]

wherein A, R and R¹–R¹¹ are as defined above.

The present invention also provides a compound of the formula:

[Structure: oxazolo-fused ring with R¹-A, R, R², R³, R⁴, R⁵, R⁶ substituents, O, C=O]

wherein A, R and R¹–R¹¹ are as defined above.

The present invention also provides a compound of the formula:

[Structure: oxadiazolo-fused ring with R¹-A, R², R³, R⁴, R⁵, R⁶ substituents, N-N, O, C=O]

wherein A, R and R¹–R¹¹ are as defined above.

The present invention also provides a compound of the formula:

[Structure: thiadiazolo-fused ring with R¹-A, R², R³, R⁴, R⁵, R⁶ substituents, N-N, S, C=O]

wherein A, R and R¹–R¹¹ are as defined above.

The present invention also provides a compound of the formula:

[Structure: oxazolo-sulfonyl-fused ring with R¹-A, R, R², R⁴ substituents, O, S(=O)₂, C=O]

wherein A, R and R¹–R¹¹ are as defined above.

The present invention also provides a compound of the formula:

[Structure: thiazolo-sulfonyl-fused ring with R¹-A, R, R², R⁴ substituents, S, S(=O)₂, C=O]

wherein A, R and R¹–R¹¹ are as defined above.

The present invention also provides a compound of the formula:

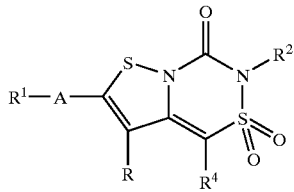

wherein A, R and $R^1$–$R^{11}$ are as defined above.

The present invention also provides a compound of the formula:

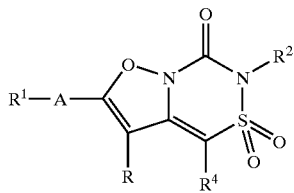

wherein A, R and $R^1$–$R^{11}$ are as defined above.

A compound of the invention may include any $R^1$ selected from the group consisting of hydrogen, ($C_1$–$C_6$)alkyl-, ($C_2$–$C_6$)alkenyl-, ($C_2$–$C_6$)alkynyl-.

A compound of the invention may include any $R^1$ selected from ($C_3$–$C_{10}$)cycloalkyl-, ($C_6$–$C_{10}$)aryl-, ($C_1$–$C_{10}$)heterocyclyl, ($C_1$–$C_{10}$)heteroaryl-.

A compound of the invention may include any $R^1$ selected from ($C_3$–$C_{10}$)cycloalkyl-($C_1$–$C_6$)alkyl-, ($C_6$–$C_{10}$)aryl-($C_1$–$C_6$)alkyl-, ($C_1$–$C_{10}$)heterocyclyl-($C_1$–$C_6$)alkyl-, ($C_1$–$C_{10}$)heteroaryl, ($C_1$–$C_6$)alkyl-, ($C_3$–$C_{10}$)cycloalkyl-($C_2$–$C_6$)alkenyl-, ($C_6$–$C_{10}$)aryl-($C_2$–$C_6$)alkenyl-, ($C_1$–$C_{10}$)heterocyclyl-($C_2$–$C_6$)alkenyl-, ($C_1$–$C_{10}$)heteroaryl-($C_2$–$C_6$)alkenyl-, ($C_3$–$C_{10}$)cycloalkyl-($C_2$–$C_6$)alkenyl-, ($C_6$–$C_{10}$)aryl-($C_2$–$C_6$)alkynyl-, ($C_1$–$C_{10}$)heterocyclyl-($C_2$–$C_6$)alkynyl-, and ($C_1$–$C_{10}$)heteroaryl-($C_2$–$C_6$)alkynyl-.

A compound of the invention may include any $R^1$ selected from ($C_6$–$C_{10}$)aryl-($C_1$–$C_6$)alkyl-, ($C_1$–$C_{10}$)heterocyclyl-($C_1$–$C_6$)alkyl-, ($C_1$–$C_{10}$)heteroaryl-($C_1$–$C_6$)alkyl-, ($C_6$–$C_{10}$)aryl-($C_2$–$C_6$)alkynyl-, ($C_1$–$C_{10}$)heterocyclyl-($C_2$–$C_6$)alkynyl-, and ($C_6$–$C_{10}$)aryl-($C$–$C_6$)alkynyl-.

A compound of the invention may include any $R^1$ optionally substituted with one to three suitable substituents selected from the group consisting of hydrogen, halogen, hydroxy, —CN, ($C_1$–$C_4$)alkyl-, ($C_1$–$C_4$)alkoxy-, $CF_3$—, $CF_3O$—, ($C_6$–$C_{10}$)aryl-, ($C_1$–$C_{10}$) heteroaryl-($C_1$–$C_4$)alkyl-$C_1$–$C_4$)alkyl-, ($C_5$–$C_{10}$)heteroaryl-($C_1$–$C_4$)alkyl-, HO(C=O)—, ($C_1$–$C_4$)alkyl-(O)(C=O)—, ($C_1$–$C_4$)alkyl-O)($C_1$–$C_4$)alkyl-, ($C_1$–$C_4$)alkyl-(C=O)—, ($C_1$–$C_4$)alkyl-(C=O)($C_1$–$C_4$)alkyl-, —(S=O)R, —($SO_2$)R, and $NR^7R^8$ wherein $R^7$ and $R^8$ are independently selected from hydrogen, ($C_1$–$C_6$)alkyl;

A compound of the invention may include any $R^1$ selected from ($C_6$–$C_{10}$)aryl-($C_1$–$C_6$)alkyl-, ($C_1$–$C_{10}$)heterocyclyl-($C_1$–$C_6$)alkyl-, ($C_1$–$C_{10}$)heteroaryl-($C_1$–$C_6$)alkyl-, ($C_6$–$C_{10}$)alkyl-, ($C_2$–$C_6$)alkynyl-, ($C_1$–$C_{10}$)heterocyclyl-($C_2$–$C_6$)alkynyl-, and ($C_1$–$C_{10}$)heteroaryl-($C_2$–$C_6$)alkynyl-; and $R^1$ is optionally substituted with one to three suitable substituents selected from the group consisting of hydrogen, halogen, hydroxy, —CN, ($C_1$–$C_4$)alkyl-, ($C_1$–$C_4$)alkoxy-, $CF_3$—, $CF_3O$—, ($C_6$–$C_{10}$)aryl-, ($C_1$–$C_{10}$)heteroaryl-, ($C_6$–$C_{10}$)aryl-($C_1$–$C_4$)alkyl-, ($C_5$–$C_{10}$)heteroaryl-($C_1$–$C_4$)alkyl-, HO(C=O)—, ($C_1$–$C_4$)alkyl-(O)(C=O)—, ($C_1$–$C_4$)alkyl-(O)(C=O)($C_1$–$C_4$)alkyl-, ($C_1$–$C_4$)alkyl-(C=O)—, ($C_1$–$C_4$)alkyl-(C=O)($C_1$–$C_4$)alkyl-, —(S=O)R, —($SO_2$)R, and $NR^7R^8$ wherein $R^7$ and $R^8$ are independently selected from hydrogen, ($C_1$–$C_6$)alkyl.

A compound of the invention may include any $R^1$ is selected from ($C_6$–$C_{10}$)aryl-($C_1$–$C_6$)alkyl- and ($C_1$–$C_{10}$)heterocyclyl-($C_1$–$C_6$)alkyl-, and $R^1$ is optionally substituted with one to three suitable substituents selected from the group consisting of hydrogen, halogen, hydroxy, —CN, ($C_1$–$C_4$)alkyl-, ($C_1$–$C_4$)alkoxy-, HO(C=O)—, and ($C_1$–$C_4$)alkyl-(C=O)(O)—.

A compound of the invention may include any $R^2$ selected from the group consisting of hydrogen, ($C_1$–$C_6$)alkyl-, ($C_2$–$C_6$)alkenyl-, ($C_2$–$C_6$)alkynyl-.

A compound of the invention may include any $R^2$ selected from ($C_3$–$C_{10}$)cycloalkyl-, ($C_6$–$C_{10}$)aryl-, ($C_1$–$C_{10}$)heterocyclyl, ($C_1$–$C_{10}$)heteroaryl-.

A compound of the invention may include any $R^2$ selected from ($C_3$–$C_{10}$)cycloalkyl-($C_1$–$C_6$)alkyl-, ($C_6$–$C_{10}$)aryl-($C_1$–$C_6$)alkyl-, ($C_1$–$C_{10}$)heterocyclyl-($C_1$–$C_6$)alkyl-, ($C_1$–$C_{10}$)heteroaryl-($C_1$–$C_6$)alkyl-, ($C_3$–$C_{10}$)cycloalkyl-($C_2$–$C_6$)alkenyl-, ($C_6$–$C_{10}$)aryl-($C_2$–$C_6$)alkenyl-, ($C_1$–$C_{10}$)heterocyclyl-($C_2$–$C_6$)alkenyl-, ($C_6$–$C_{10}$)aryl-($C_2$–$C_6$)alkynyl-, ($C_1$–$C_{10}$)heteroaryl-($C_2$–$C_6$)alkenyl-, ($C_3$–$C_{10}$)cycloalkyl-($C_2$–$C_6$)alkynyl-, ($C_6$–$C_{10}$)aryl-($C_2$–$C_6$)alkynyl-, ($C_1$–$C_{10}$)heterocycl-($C_2$–$C_6$)alkynyl-, and ($C_1$–$C_{10}$)heteroaryl-($C_2$–$C_6$)alkynyl-.

A compound of the invention may include any $R^2$ ($C_6$–$C_{10}$)aryl-($C_1$–$C_6$)alkyl-, ($C_1$–$C_{10}$)heterocyclyl-($C_1$–$C_6$) alkyl-, ($C_1$–$C_{10}$)heteroaryl-($C_1$–$C_6$)alkyl-, ($C_6$–$C_{10}$)aryl-($C_2$–$C_6$)alkynyl-, ($C_1$–$C_{10}$)heterocyclyl-($C_2$–$C_6$)alkynyl-, and ($C_6$–$C_{10}$)aryl-($C_2$–$C_6$)alkynyl-.

A compound of the invention may include any $R^2$ optionally substituted with one to three suitable substituents selected from the group consisting of hydrogen, halogen, hydroxy, —CN, —($C_1$–$C_4$)alkyl, —($C_1$–$C_4$)alkoxy, —$CF_3$, $CF_3O$—, —($C_6$–$C_{10}$)aryl, —($C_1$–$C_{10}$)heteroaryl-($C_6$–$C_{10}$) aryl-($C_1$–$C_4$)alkyl-, ($C_1$–$C_{10}$)heteroaryl-($C_1$–$C_4$)alkyl-, —(C=O)—OH, —O(C=O)—($C_1$–$C_4$) alkyl, —(C=O)—O—($C_1$–$C_4$)alkyl, —(S=O)R, —($SO_2$)R, and $NR^7R^8$, wherein $R^7$ and $R^8$ are independently selected from hydrogen, ($C_1$–$C_6$)alkyl.

A compound of the invention may include any $R^2$ such as ($C_6$–$C_{10}$)aryl-($C_1$–$C_6$)alkyl-, ($C_1$–$C_{10}$)heterocyclyl-($C_1$–$C_6$) alkyl-, ($C_1$–$C_{10}$)heteroaryl-($C_1$–$C_6$)alkyl-, ($C_6$–$C_{10}$)aryl-($C_2$–$C_6$)alkynyl-, ($C_1$–$C_{10}$)heterocyclyl-($C_2$–$C_6$)alkynyl-, and ($C_1$–$C_{10}$)heteroaryl-($C_2$–$C_6$)alkynyl-; and $R^2$ is optionally substituted with one to three suitable substituents selected from the group consisting of hydrogen, halogen, hydroxy, —CN, —($C_1$–$C_4$)alkyl, —($C_1$–$C_4$)alkoxy, —$CF_3$, $CF_3O$—, —($C_6$–$C_{10}$)aryl, —($C_1$–$C_{10}$)heteroaryl, ($C_6$–$C_{10}$) aryl-($C_1$–$C_4$)alkyl-, ($C_1$–$C_{10}$)heteroaryl, ($C_1$–$C_4$)alkyl-, —(C=O)—OH, —O(C=O)—($C_1$–$C_4$)alkyl, —(C=O)—O—($C_1$–$C_4$)alkyl, —(S=O)R, —($SO_2$) R, and $NR^7R^8$, wherein $R^7$ and $R^8$ are independently selected from hydrogen, ($C_1$–$C_6$)alkyl.

A compound of the invention may include any $R^2$ such as ($C_6$–$C_{10}$)aryl-($C_1$–$C_6$)alkyl-, and $R^2$ is optionally substituted with one to three suitable substituents selected from the group consisting of hydrogen, halogen, hydroxy, —CN, —($C_1$–$C_4$)alkyl, —($C_1$–$C_4$)alkoxy, —(C=O)—OH, and —O(C=O)—($C_1$–$C_4$)alkyl.

A compound of the invention may include any $R^3$ selected from the group consisting of hydrogen, ($C_1$–$C_6$)alkyl-, ($C_2$–$C_6$)alkenyl-, ($C_2$–$C_6$)alkynyl-.

A compound of the invention may include any $R^4$ such as ($C_1$–$C_6$)alkyl-.

A compound of the invention may include any $R^5$ selected from the group consisting of hydrogen, $(C_1-C_6)$alkyl-, $(C_2-C_6)$alkenyl-, $(C_2-C_6)$alkynyl-.

A compound of the invention may include any $R^6$ selected from the group consisting of hydrogen, $(C_1-C_6)$alkyl-, $(C_2-C_6)$alkenyl-, $(C_2-C_6)$alkynyl-.

The present invention provides a compound selected from:

- 4-[6-(4-Methoxy-benzylcarbamoyl)-1-oxo-pyrrolo[1,2-c]pyrimidin-2-ylmethyl]-benzoic acid
- 2-(3,4-Difluoro-benzyl)-1-oxo-1,2-dihydro-pyrrolo[1,2-c]pyrimidine-6-carboxylic acid 4-methoxy-benzylamide
- 4-[6-(3-Methoxy-benzylcarbamoyl)-1-oxo-pyrrolo[1,2-c]pyrimidin-2-ylmethyl]-benzoic acid
- 2-(3,4-Difluoro-benzyl)-1-oxo-1,2-dihydro-pyrrolo[1,2-c]pyrimidine-6-carboxylic acid 3-methoxy-benzylamide
- 4-{6-[3-(4-Methoxy-phenyl)-prop-1-ynyl]-1-oxo-pyrrolo[1,2-c]pyrimidin-2-ylmethyl}-benzoic acid
- 2-(3,4-Difluoro-benzyl)-6-[3-(4-methoxy-phenyl)-prop-1-ynyl]-2H-pyrrolo[1,2-c]pyrimidin-1-one
- 4-{6-[3-(3-Methoxy-phenyl)-prop-1-ynyl]-1-oxo-pyrrolo[1,2-c]pyrimidin-2-ylmethyl}-benzoic acid
- 2-(3,4-Difluoro-benzyl)-6-[3-(3-methoxy-phenyl)-prop-1-ynyl]-2H-pyrrolo[1,2-c]pyrimidin-1-one or pharmaceutically acceptable salts thereof.

The invention further provides a compound selected from the group consisting of:

- 4-[2-(4-Methoxy-benzylcarbamoyl)-8-methyl-5,7,7-trioxo-7H-7$\lambda^6$-oxazolo[3,2-d][1,2,4]thiadiazin-6-ylmethyl]-benzoic acid
- 6-(3,4-Difluoro-benzyl)-8-methyl-5,7,7-trioxo-6,7-dihydro-5H-7$\lambda^6$-oxazolo[3,2-d][1,2,4]thiadiazine-2-carboxylic acid 4-methoxy-benzylamide
- 4-[2-(3-Methoxy-benzylcarbamoyl)-8-methyl-5,7,7-trioxo-7H-7$\lambda^6$-oxazolo[3,2-d][1,2,4]thiadiazin-6-ylmethyl]-benzoic acid
- 6-(3,4-Difluoro-benzyl)-8-methyl-5,7,7-trioxo-6,7-dihydro-5H-7$\lambda^6$-oxazolo[3,2-d][1,2,4]thiadiazine-2-carboxylic acid 3-methoxy-benzylamide
- 4-[2-(4-Methoxy-benzylcarbamoyl)-7-methyl-4,6,6-trioxo-6H-1,6$\lambda^6$-dithia-3a,5-diaza-inden-5-ylmethyl]-benzoic acid
- 5-(3,4-Difluoro-benzyl)-7-methyl-4,6,6-trioxo-5,6-dihydro-4H-1,6$\lambda^6$-dithia-3a,5-diaza-inden-2-carboxylic acid 4-methoxy-benzylamide
- 4-[2-(3-Methoxy-benzylcarbamoyl)-7-methyl-4,6,6-trioxo-6H-1,6$\lambda^6$-dithia-3a,5-diaza-inden-5-ylmethyl]-benzoic acid
- 5-(3,4-Difluoro-benzyl)-7-methyl-4,6,6-trioxo-5,6-dihydro-4H-1,6$\lambda^6$-dithia-3a,5-diaza-inden-2-carboxylic acid 3-methoxy-benzylamide
- 4-{2-[3-(4-Methoxy-phenyl)-prop-1-ynyl]-8-methyl-5,7,7-trioxo-7H-7$\lambda^6$-oxazolo[3,2-d][1,2,4]thiadiazin-6-ylmethyl}-benzoic acid
- 6-(3,4-Difluoro-benzyl)-2-[3-(4-methoxy-phenyl)-prop-1-ynyl]-8-methyl-7,7-dioxo-6,7-dihydro-7$\lambda^6$-oxazolo[3,2-d][1,2,4]thiadiazin-5-one
- 4-{2-[3-(3-Methoxy-phenyl)-prop-1-ynyl]-8-methyl-5,7,7-trioxo-7H-7$\lambda^6$-oxazolo[3,2-d][1,2,4]thiadiazin-6-ylmethyl}-benzoic acid
- 6-(3,4-Difluoro-benzyl)-2-[3-(3-methoxy-phenyl)-prop-1-ynyl]-8-methyl-7,7-dioxo-6,7-dihydro-7$\lambda^6$-oxazolo[3,2-d][1,2,4]thiadiazin-5-one
- 4-{2-[3-(4-Methoxy-phenyl)-prop-1-ynyl]-7-methyl-4,6,6-trioxo-6H-1,6$\lambda^6$-dithia-3a,5-diaza-inden-5-ylmethyl}-benzoic acid
- 5-(3,4-Difluoro-benzyl)-2-[3-(4-methoxy-phenyl)-prop-1-ynyl]-7-methyl-6,6-dioxo-5,6-dihydro-1,6$\lambda^6$-dithia-3a,5-diaza-inden-4-one
- 4-{2-[3-(3-Methoxy-phenyl)-prop-1-ynyl]-7-methyl-4,6,6-trioxo-6H-1,6$\lambda^6$-dithia-3a,5-diaza-inden-5-ylmethyl}-benzoic acid
- 5-(3,4-Difluoro-benzyl)-2-[3-(3-methoxy-phenyl)-prop-1-ynyl-7-methyl-6,6-dioxo-5,6-dihydro-1,6$\lambda^6$-dithia-3a,5-diaza-inden-4-one Still further, the invention provides a compound selected from:

- 4-[2-(4-Methoxy-benzylcarbamoyl)-5-oxo-7,8-dihydro-imidazo[1,2-c]pyrimidin-6-ylmethyl]-benzoic acid
- 6-(3,4-Difluoro-benzyl)-5-oxo-5,6,7,8-tetrahydro-imidazo[1,2-c]pyrimidine-2-carboxylic acid 4-methoxy-benzylamide
- 4-[2-(3-Methoxy-benzylcarbamoyl)-5-oxo-7,8-dihydro-imidazo[1,2-c]pyrimidin-6-ylmethyl]-benzoic acid
- 6-(3,4-Difluoro-benzyl)-5-oxo-5,6,7,8-tetrahydro-imidazo[1,2-c]pyrimidine-2-carboxylic acid 3-methoxy-benzylamide
- 4-{2-[3-(4-Methoxy-phenyl)-prop-1-ynyl]-5-oxo-7,8-dihydro-imidazo[1,2-c]pyrimidin-6-ylmethyl}-benzoic acid
- 6-(3,4-Difluoro-benzyl)-2-[3-(4-methoxy-phenyl)-prop-1-ynyl]-7,8-dihydro-6H-imidazo[1,2-c]pyrimidin-5-one
- 4-{2-[3-(3-Methoxy-phenyl)-prop-1-ynyl]-5-oxo-7,8-dihydro-imidazo[1,2-c]pyrimidin-6-ylmethyl}-benzoic acid
- 6-(3,4-Difluoro-benzyl)-2-[3-(3-methoxy-phenyl)-prop-1-ynyl]-7,8-dihydro-6H-imidazo[1,2-c]pyrimidin-5-one.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)) salts.

The invention also relates to base addition salts of formula I. The chemical bases that may be used as reagents to prepare pharmaceutically acceptable base salts of those compounds of or a bond that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Certain compounds of the present invention exist in unsolvated forms as well as solvated forms, including hydrated forms. In general, the solvated forms, including hydrated forms, are equivalent to unsolvated forms and are encompassed within the scope of the present invention.

The term "alkyl", as used herein, unless otherwise indicated, includes saturated monovalent hydrocarbon radicals having straight, branched or cyclic moieties or combinations thereof. Alkyl groups, wherever they occur, may be optionally substituted by a suitable substituent.

The term "alkenyl", as used herein, unless otherwise indicated, includes hydrocarbon radicals containing at least one olefin linkage and having straight, branched or cyclic moieties or combinations thereof.

The term "alkynyl", as used herein, unless otherwise indicated, includes hydrocarbon radicals containing at least one carbon-carbon triple bond linkage and having straight, branched or cyclic moieties or combinations thereof.

The term "alkoxy", as used herein, includes O-alkyl groups wherein "alkyl" is as defined above.

The term "halo", as used herein, unless otherwise indicated, includes fluorine, chlorine, bromine or iodine, preferably fluorine or chlorine.

The term "(C=O)" as used herein refers to a carbonyl group. Used in common with a nitrogen atom the group refers to amide. Used in common with an oxygen atom, the group refers to carboxylic acid derivatives.

The term "aryl", as used herein, unless otherwise indicated, includes an organic radical derived from an aromatic hydrocarbon by removal of one or more hydrogens, such as phenyl, naphthyl indanyl or tetrahydronaphthyl; optionally substituted by 1 to 3 suitable substituents such as fluoro, chloro, cyano, nitro, trifluoromethyl, $(C_1-C_6)$alkoxy, $(C_6-C_{10})$aryloxy, $(C_3-C_6)$cycloalkyloxy, trifluoromethoxy, difluoromethoxy, (C=O), O—(C=O), (C=O)—O, or $(C_1-C_6)$alkyl. The term "aryl" also encompasses fused aryl groups, including but not limited to pentalene, inden, naphthalene, azulene, and fluorene.

The term "cycloalkyl", as used herein, unless otherwise indicated, includes a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1–2 double bonds and optionally substituted by 1 to 3 suitable substituents as defined below such as fluoro, chloro, trifluoromethyl, $(C_1-C_4)$alkoxy, $(C_6-C_{10})$aryloxy, trifluoromethoxy, difluoromethoxy (C=O), O—(C=O), (C=O)—O, or $(C_1-C_4)$alkyl, more preferably fluoro, chloro, methyl, ethyl and methoxy. The term "cycloalkyl" also includes bridged cycloalkyl groups, including, without limitation, norbornyl and adamantanyl, as well as spiro cycloalkyl groups, i.e., multi-ring systems joined by a single atom, such as:

The term "heteroaryl", as used herein, unless otherwise indicated, includes an organic radical derived from an aromatic heterocyclic compound by removal of one or more hydrogens, such as benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl, and triazolyl, wherein said heteroaryl is optionally substituted on any of the ring carbon atoms capable of forming an additional bond by one or two suitable substituents such as F, Cl, Br, CN, OH, $(C_1-C_4)$ alkyl, $(C_1-C_4)$perfluoroalkyl, $(C_1-C_4)$perfluoroalkoxy, $(C_1-C_4)$alkoxy, (C=O), O—(C=O), (C—O)—O, and $(C_3-C_8)$cycloalkyloxy. The heteroaryl may also be optionally interrupted by (C=O) and (C=O)—O. The foregoing groups, as derived from the compounds listed above, may be C-attached or N-attached where such is possible. For instance, a group derived from pyrrole may be pyrrol-1-yl (N-attached) or pyrrol-3-yl (C-attached). The term "heteroaryl", therefore includes aromatic heterocycles having one or more heteroatoms, such as N, O, or S. In addition, "heteroaryl" also refers to fused heteroaryl ring systems, including without limitation, benzofuran, isobenzofuran, benzothiofuran, isobenzothiofuran, indole, indolenine, 2 isobenzazole, 1,5-pyrindine, pyrano[3,4-b]-pyrrole, isoindazole, indoxazine, benzoxazole, anthranil, benzopyran, coumarin, chromone, isocoumarin, 2,3-benzopyrone, quinoline, isoquinoline, cinnoline, quinazoline, naphthyridine, pyrido[3,4-b]-pyridine, pyrido[3,2-b]pyridine, pyrido[4,3-b]pyridine, and benzoxazine.

The term "heterocyclyl", as used herein, unless otherwise indicated, includes an organic radical derived from a non-aromatic heterocyclic compound by removal of one or more hydrogens, such as 3-azabicyclo[3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydrofuranyl, tetrahydropyranyl, 1,2,3,6-tetrahydropyridinyl, tetrahydrothienyl, tetrahydrothiopyranyl, thiomorpholinyl, thioxanyl, and trithianyl. The foregoing groups, as derived from the compounds listed above, may be C-attached or N-attached where such is possible. For example, a group derived from piperidine may be piperidin-1-yl (N-attached) or piperidin-4-yl (C-attached). The foregoing groups, as derived from the compounds listed above, may be optionally substituted where such is possible by a suitable substituent, such as oxo F, Cl, Br, CN, OH, $(C_1-C_4)$alkyl, $(C_1-C_4)$ perfluoroalkyl, $(C_1-C_4)$perfluoroalkoxy, $(C_1-C_4)$alkoxy, (C=O), O—(C=O), (C=O)—O, and $(C_3-C_8)$ cycloalkyloxy. The term "heterocyclyl", therefore includes heterocycles having one or more heteroatoms, such as N, O, or S. In addition, a "heterocyclyl" group may be optionally interrupted by one or more (C=O) or O—(C=O).

"A suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, carboxy groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, an arylsulfonyl groups and the like.

The compounds of the invention possess a fused bicyclic ring structure of the formula:

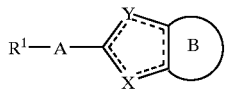

wherein dashed lines within the rings of the fused system represent optional double bonds. The position of a double bond within the ring system will depend, at least in part, on the nature of the atom at any given position in the ring system. For example, it will be understood that if Y is O, then neither bond to which Y is attached in the ring system depicted above may be a double bond.

Some compounds of formula I contain chiral centers and therefore exist in different enantiomeric forms. This invention relates to all optical isomers, enantiomers, diasteriomers and stereoisomers of the compounds of or a bond and mixtures thereof. The compounds of the invention also exist in different tautomeric forms. This invention relates to all tautomers of formula I. The various ratios of the tautomers in solid and liquid form is dependent on the various substituents on the molecule as well as the particular crystallization technique used to isolate a compound.

Certain of the compounds of the invention possess one or more chiral centers, and each center may exist in the R or S configuration. An invention compound includes any diastereomeric, enantiomeric, or epimeric form of the compound, as well as mixtures thereof.

Additionally, certain invention compounds may exist as geometric isomers such as the entgegen (E) and zusammen (Z) isomers of 1,2-disubstituted alkenyl groups or cis and trans isomers of disubstituted cyclic groups. An invention compound includes any cis, trans, syn, anti, entgegen (E), or zusammen (Z) isomer of the compound, as well as mixtures thereof.

Certain invention compounds can exist as two or more tautomeric forms. Tautomeric forms of the invention compounds may interchange, for example, via enolization/deenolization, 1,2-hydride, 1,3-hydride, or 1,4-hydride shifts, and the like. An invention compound includes any tautomeric form of the compound, as well as mixtures thereof.

Some compounds of the present invention have alkenyl groups, which may exist as entgegen or zusammen conformations, in which case all geometric forms thereof, both entgegen and zusammen, cis and trans, and mixtures thereof, are within the scope of the present invention.

Some compounds of the present invention have cycloalkyl groups, which may be substituted at more than one carbon atom, in which case all geometric forms thereof, both cis and trans, and mixtures thereof, are within the scope of the present invention.

The present invention also relates to a pharmaceutical composition for the treatment of a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers and other diseases characterized by metalloproteinase activity in a mammal, including a human, comprising an amount of a compound of formula (I) or a pharmaceutically acceptable salt thereof effective in such treatments and a pharmaceutically acceptable carrier.

The present invention also relates to a pharmaceutical composition for the inhibition of matrix metalloproteinases or other metalloproteinases involved in matrix degradation, in a mammal, including a human, comprising an effective amount of a compound of formula (I) or a pharmaceutically acceptable salt thereof.

The present invention also relates to a method for treating a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers and other diseases characterized by matrix metalloproteinase activity in a mammal, including a human, comprising administering to said mammal an amount of a compound of formula (I) or a pharmaceutically acceptable salt thereof effective in treating such a condition.

The present invention also relates to a method for the inhibition of matrix metalloproteinases or other metalloproteinases involved in matrix degradation, in a mammal, including a human, comprising administering to said mammal an effective amount of a compound of formula (I) or a pharmaceutically acceptable salt thereof.

The present inventors have also discovered that it is possible to identify inhibitors of formula (I) with differential metalloprotease activity (preferably MMP-13 inhibitory activity). One group of preferred inhibitors of formula (I) the inventors may beable to identify include those which selectively inhibit MMP-13 preferentially over MMP-1. The compounds of the invention also possess selectivity over a related group of enzymes known as reprolysins, such as TACE and aggrecanase. Another group of preferred inhibitors of formula (I) the inventors may beable to identify include those which selectively inhibit MMP-13 preferentially over MMP-1 and MMP-14. Another group of preferred inhibitors of formula (I) the inventors may beable to identify include those which selectively inhibit MMP-13 preferentially over MMP-1 and 12. Another group of preferred inhibitors of formula (I) the inventors may beable to identify include those which selectively inhibit MMP-13 preferentially over MMP-1, 12 and 14. Another group of preferred inhibitors of formula (I) the inventors may beable to identify include those which selectively inhibit MMP-13 preferentially over MMP-1, 2, 3, 7, 9 and 14. Most preferred compounds of the invention selectively inhibit MMP-13 preferentially over MMP-1, 2, 3, 7, 9, 12 and 14 and mammalian reprolysins.

The present invention also relates to a method for treating a medical condition of the type that is characterized by the destruction of articular cartilage in a mammalian subject, which method comprises administering to the subject having said condition a therapeutically effective amount of a suitably substituted fused bicyclic, wherein said suitably substituted fused pyrimidine exhibits: i) a MMP-13 $IC_{50}$ of less than about 100 nM (more preferably 50 nM, most preferably less than 20 nM), said MMP-13 $IC_{50}$ measured by an recombinant MMP-13 assay, ii) a MMP-1 $IC_{50}$ of greater than about 200 nM (more preferably greater than 500 nM, most preferably greater than 1 $\mu$M), said MMP-1 $IC_{50}$ measured by a recombinant MMP-1 assay; and iii) a MMP-14 $IC_{50}$ of greater than about 200 nM (more preferably greater than 500 nM, most preferably greater than 1 $\mu$M), said MMP-14 $IC_{50}$ measured by a recombinant MMP-14 assay.

The present invention also relates to a method for treating the destruction of articular cartilage wherein said fused bicyclic additionally exhibits a MMP-12 $IC_{50}$ of greater than about 100 nM (more preferably greater than 200 nM, most preferably greater than 500 nM), said MMP-12 $IC_{50}$ measured by a recombinant MMP-12 assay.

The present invention also relates to a method for treating the destruction of articular cartilage wherein said fused bicyclic additionally exhibits i) a MMP-2 $IC_{50}$ of greater than about 200 nM (more preferably greater than 500 nM, most preferably greater than 1 $\mu$M), said MMP-2 $IC_{50}$ measured by a recombinant MMP-2 assay, ii). a MMP-3 $IC_{50}$ of greater than about 200 nM (more preferably greater than 500 nM, most preferably greater than 1 $\mu$M), said MMP-3 $IC_{50}$ measured by a recombinant MMP-3 assay, iii) a MMP-7 $IC_{50}$ of greater than about 200 nM (more preferably greater than 500 nM, most preferably greater than 1 $\mu$M), said MMP-7 $IC_{50}$ measured by a recombinant MMP-7 assay, and iv) a MMP-9 $IC_{50}$ of greater than about 200 nM (more preferably greater than 500 nM, most preferably greater than 1 $\mu$M), said MMP-9 $IC_{50}$ measured by a recombinant MMP-9 assay.

The term "treating", as used herein, refers to reversing, alleviating, inhibiting the progression of, or preventing the disorder or condition to which such term applies, or one or more symptoms of such disorder or condition. The term "treatment", as used herein, refers to the act of treating, as "treating" is defined immediately above.

"Connective tissue disorders" as used herein refers to disorders such as degenerative cartilage loss following traumatic joint injury, osteoarthritis, osteoporosis, Paget's disease, loosening of artificial joint implants, periodontal disease and gingivitis.

"Destruction of articular cartilage" as used herein refers to connective tissue disorders resulting in articular cartilage destruction, preferably joint injury, reactive arthritis, acute pyrophosphate arthritis (pseudogout), psoriatic arthritis, or juvenile rheumatoid arthritis, more preferably osteoarthritis.

"Inflammatory disorders" as used herein refers to disorders such as rheumatoid arthritis, ankylosing spondylitis, psoriatic arthritis, psoriasis, chondrocalcinosis, gout, inflammatory bowel disease, ulcerative colitis, Crohn's disease and cachexia.

"Immunology/allergy disorders" as used herein refers to disorders such as organ transplant toxicity, allergic reactions, allergic contact hypersensitivity, autoimmune disorders such as those disorders associated with granulomatous inflammation/tissue remodeling (such as asthma), immunosuppression and sarcoid.

"Infectious diseases," including those mediated by viruses, bacteria, fungi or mycobacterial infection, as used herein refers to disorders such as septic arthritis, AIDS, fever; Prion diseases, myasthenia gravis, Malaria, sepsis, hemodynamic shock, and septic shock.

"Respiratory diseases" as used herein refers to disorders such as chronic obstructive pulmonary disease (including emphysema), acute respiratory distress syndrome, asthma, hyperoxic alveolar injury and idiopathic pulmonary fibrosis and other fibrotic lung diseases.

"Cardiovascular diseases" as used herein refers to disorders such as atherosclerosis including atherosclerotic plaque rupture; aortic aneurysm including abdominal aortic aneurysm and brain aortic aneurysm; congestive heart failure; myocardial and cerebral infarction; stroke; cerebral ischemia; coagulation and acute phase response; left ventricular dilation; post ischemic reperfusion injury; angiofibromas; hemangiomas; and restenosis.

"Eye diseases" as used herein refers to disorders such as aberrant angiogenesis, ocular angiogenesis, ocular inflammation, keratoconus, Sjogren's syndrome, myopia, ocular tumors, corneal graft rejection, corneal injury, neovascular glaucoma, corneal ulceration, corneal scarring, macular degeneration (including "Age Related Macular Degeneration (ARMD) including both wet and dry forms), proliferative vitreoretinopathy and retinopathy of prematurity.

"Metabolic diseases" as used herein refers to disorders such as diabetes (including non-insulin dependent diabetes mellitus, diabetic retinopathy, insulin resistance, diabetic ulceration).

"Central Nervous System" (CNS) disorders as used herein refers to disorders such as head trauma, spinal cord injury, Inflammatory diseases of the central nervous system, neurodegenerative disorders (acute and chronic), Alzheimer's disease, demyelinating diseases of the nervous system, Huntington's disease, Parkinson's disease, peripheral neuropathy, pain, cerebral amyloid angiopathy, nootropic or cognition enhancement, amyotrophic lateral sclerosis, multiple sclerosis, migraine, depression and anorexia.

"Liver/Kidney diseases" as used herein refers to disorders such as nephrotic syndromes such as glomerulonephritis and glomerular disease of the kidney, proteinuria, cirrhosis of the liver and interstitial nephritis.

"Reproductive Health disorders" as used herein refers to disorders such as endometriosis, contraception (male/female), dysmenorrhea, dysfunctional uterine bleeding, premature rupture of fetal membranes and abortifactant.

"Gastric disorders" as used herein refers to disorders such as colonic anastomosis and gastric ulcers.

"Skin disorders" as used herein refers to disorders such as skin aging, pressure sores, psoriasis, eczema, dermatitis, radiation damage, tissue ulceration, decubital ulcers, epidermolysis bullosa, abnormal wound healing (topical and oral formulations), burns and scleritis.

"Cancers" as used herein refers to disorders such as solid tumor cancer including colon cancer, breast cancer, lung cancer and prostrate cancer, tumor invasion, tumor growth tumor metastasis, cancers of the oral cavity and pharynx (lip, tongue, mouth, pharynx), esophagus, stomach, small intestine, large intestine, rectum, liver and biliary passages, pancreas, larynx, lung, bone, connective tissue, skin, cervix uteri, corpus endometrium, ovary, testis, bladder, kidney, and other urinary tissues, eye brain and central nervous system, thyroid and other endocrine gland, Hodgkin's disease, non-Hodgkin's lymphomas, multiple myeloma, and hematopoietic malignancies including leukemias and lymphomas including lymphocytic, granulocytic and monocytic.

The subject invention also includes isotopically-labelled compounds, which are identical to those recited in Formula (I) but for the fact that one or more atoms are replaced by an atom having an atomic mass or mass number different from the atomic mass or mass number usually found in nature. Examples of isotopes that may be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labelled compounds of Formula (I) of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

This invention also encompasses pharmaceutical compositions containing prodrugs of compounds of the formula (I). This invention also encompasses methods of treating or preventing disorders that may be treated or prevented by the inhibition of matrix metalloproteinases or the inhibition of mammalian reprolysin comprising administering prodrugs of compounds of the formula (I). Compounds of formula (I) having free amino, amido, hydroxy, sulfonamide or carboxylic groups may be converted into prodrugs. Prodrugs include compounds wherein an amino acid residue, or a polypeptide chain of two or more (e.g., two, three or four) amino acid residues which are covalently joined through peptide bonds to free amido, amino, hydroxy or carboxylic acid groups of compounds of formula (I). The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, omithine and methionine sulfone. Prodrugs also include compounds wherein carbonates, carbamates, amides and alkyl esters, which are covalently, bonded to the above substituents of formula (I) through the carbonyl carbon prodrug sidechain. Prodrugs also include dimers of compounds of formula (I).

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as infliximab, D2E7 and CDP-870) and TNF receptor immunoglobulin molecules (such as etanercept), ICE inhibitors, MEKK1 inhibitors, COX-2 inhibitors such as celecoxib, rofecoxib, valdecoxib and etoricoxib; low dose methotrexate, lefunimide, steroids, glucosamines, chondrosamines/sulfates, gabapentin, A-agonists, IL-1 process and release inhibitors, IL-1 receptor antagonists such as Kineret®, CCR-1 antagonists, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, paracoxib, etoricoxib and rofecoxib, analgesics, steroids, glucosamines, chondrosamines/sulfates, gabapentin, A-agonists, IL-1 process and release inhibitors, CCR-1 antagonists, LTD-4, LTB-4 and 5-LO inhibitors, p38 kinase inhibitors and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, paclitaxel, docetaxel and alkaloids, such as vincristine, and antimetabolites such as methotrexate.

The compounds of the present invention may also be used in combination with cardiovascular agents such as calcium channel blockers (such as amlodipine and nifedipine), lipid lowering agents such as statins (such as lovastatin, atorvastatin, pravastatin and simvastatin), adrenergics such as doxazosin and terazosin; fibrates, beta-blockers, Ace inhibitors (such as captopril, lisinopril, fosinopril, enalapril and quinaprill), Angiotensin-2 receptor antagonists such as losartan and irbesartan; nitrates, CCB's, diuretics such as digitalis, and platelet aggregation inhibitors. The compounds of the present invention may also be used in combination with plaque rupture preventitive agents such as statins, zithromax, NSAIDs including aspirin, heparin, urarfarin, abciximab, TPA and platelet Inhibitors. The compounds of the present invention may also be used in combination with stroke treatment agents such as NIF, NHEI's and CCRIR antagonists.

The compounds of the present invention may also be used in combination with CNS agents such as antidepressants (such as sertraline), anti-Parkinsonian drugs (such as deprenyl, carbadopa, L-dopa, dopamine receptor agonists such as ropinirole, pergolide and pramipexole; MAOB inhibitors such as selegiline and rasagiline, catechol-O-methyltrasferase inhibitors such as tolcapone, A-2 inhibitors, dopamine reuptake inhibitors, NMDA antagonists, Nicotine agonists, NK-1 inhibitors, dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506 and rapamycin.

The compounds of the present invention may also be used in combination with agents for the treatment of respiratory diseases such as PDE-IV inhibitors, steroidals such as fluticasone, triamcinolone, budesonide, budesonide and beclomethasone, anticholinergics such as ipratropium, sympathomimetics such as salmeterol, albuterol and Xopenex, decongestants such as fexofenadine, loratadine, and cetirizine; leukotriene antagonists such as zafirlukast and motelukast; and mast cell stabilizers such as zileuton.

The compounds of the present invention may also be used in combination with agents for the treatment of skin disorders such as tretinoin, isotretinoin, steroids such as cortisone and mometasone, antibiotics such as tetracycline, antifungals such as clotrimazole, miconazole and fluconazole and PDE-IV inhibitors.

The compounds of the present invention may also be used in combination with agents for the treatment of diabetes such as insulin, including human or humanized insulin and inhaled insulin, aldose reductase inhibitors, sorbitol dehydrogenase inhibitors, antidiabetic agents such as biguanides such as metformin; glitazones, glycosidase inhibitors such as acarbose, sulfonylureas such as glimepiride and glipizide;

and thiazolidinediones such as pioglitazone, rosiglitazone and trogliazone. Preferred combinations are useful for treating the side effects of diabetes such as retinopathy, nephropathy and neuropathy, preferably retinopathy.

DETAILED DESCRIPTION OF THE INVENTION

Any invention compound is readily available, either commercially, or by synthetic methodology, well known to those skilled in the art of organic chemistry. For specific syntheses, see the examples below and the preparations of invention compound outlined in the Schemes below.

Intermediates for the synthesis of a compound of formula (I), or a pharmaceutically acceptable salt thereof, may be prepared by one of ordinary skill in the art of organic chemistry by adapting various synthetic procedures incorporated by reference above or that are well-known in the art of organic chemistry. These synthetic procedures may be found in the literature in, for example, Reagents for Organic Synthesis, by Fieser and Fieser, John Wiley & Sons, Inc, New York, 2000; Comprehensive Organic Transformations, by Richard C. Larock, VCH Publishers, Inc, New York, 1989; the series Compendium of Organic Synthetic Methods, 1989, by Wiley-Interscience; the text Advanced Organic Chemistry, 4$^{th}$ edition, by Jerry March, Wiley-Interscience, New York, 1992; or the Handbook of Heterocyclic Chemistry by Alan R. Katritzky, Pergamon Press Ltd, London, 1985, to name a few. Alternatively, a skilled artisan may find methods useful for preparing the intermediates in the chemical literature by searching widely available databases such as, for example, those available from the Chemical Abstracts Service, Columbus, Ohio, or MDL Information Systems GmbH (formerly Beilstein Information Systems GmbH), Frankfurt, Germany.

Preparations of the invention compounds may use starting materials, reagents, solvents, and catalysts that may be purchased from commercial sources or they may be readily prepared by adapting procedures in the references or resources cited above. Commercial sources of starting materials, reagents, solvents, and catalysts useful in preparing invention compounds include, for example, The Aldrich Chemical Company, and other subsidiaries of Sigma-Aldrich Corporation, St. Louis, Mo., BACHEM, BACHEM A.G., Switzerland, or Lancaster Synthesis Ltd, United Kingdom.

Syntheses of some invention compounds may utilize starting materials, intermediates, or reaction products that contain a reactive functional group. During chemical reactions, a reactive functional group may be protected from reacting by a protecting group that renders the reactive functional group substantially inert to the reaction conditions employed. A protecting group is introduced onto a starting material prior to carrying out the reaction step for which a protecting group is needed. Once the protecting group is no longer needed, the protecting group may be removed. It is well within the ordinary skill in the art to introduce protecting groups during a synthesis of a compound of formula (I), or a pharmaceutically acceptable salt thereof, and then later remove them. Procedures for introducing and removing protecting groups are known and referenced such as, for example, in Protective Groups in Organic Synthesis, 2$^{nd}$ ed., Greene T. W. and Wuts P. G., John Wiley & Sons, New York: N.Y., 1991, which is hereby incorporated by reference.

Thus, for example, protecting groups such as the following may be utilized to protect amino, hydroxyl, and other groups: carboxylic acyl groups such as, for example, formyl, acetyl, and trifluoroacetyl; alkoxycarbonyl groups such as, for example, ethoxycarbonyl, tertbutoxycarbonyl (BOC), β,β,β-trichloroethoxycarbonyl (TCEC), and β-iodoethoxycarbonyl; aralkyloxycarbonyl groups such as, for example, benzyloxycarbonyl (CBZ), para-methoxybenzyloxycarbonyl, and 9-fluorenylmethyloxycarbonyl (FMOC); trialkylsilyl groups such as, for example, trimethylsilyl (TMS) and tert-butyidimethylsilyl (TBDMS); and other groups such as, for example, triphenylmethyl (trityl), tetrahydropyranyl, vinyloxycarbonyl, orthonitrophenylsulfenyl, diphenylphosphinyl, para-toluenesulfonyl (Ts), mesyl, trifluoromethanesulfonyl, and benzyl. Examples of procedures for removal of protecting groups include hydrogenolysis of CBZ groups using, for example, hydrogen gas at 50 psi in the presence of a hydrogenation catalyst such as 10% palladium on carbon, acidolysis of BOC groups using, for example, hydrogen chloride in dichloromethane, trifluoroacetic acid (TFA) in dichloromethane, and the like, reaction of silyl groups with fluoride ions, and reductive cleavage of TCEC groups with zinc metal.

The following reaction Scheme illustrates the preparation of the compounds of the present invention. Unless otherwise indicated X, Y, A, B, R and R$^1$—R$^{11}$ in the reaction Schemes and the discussion that follows are defined above.

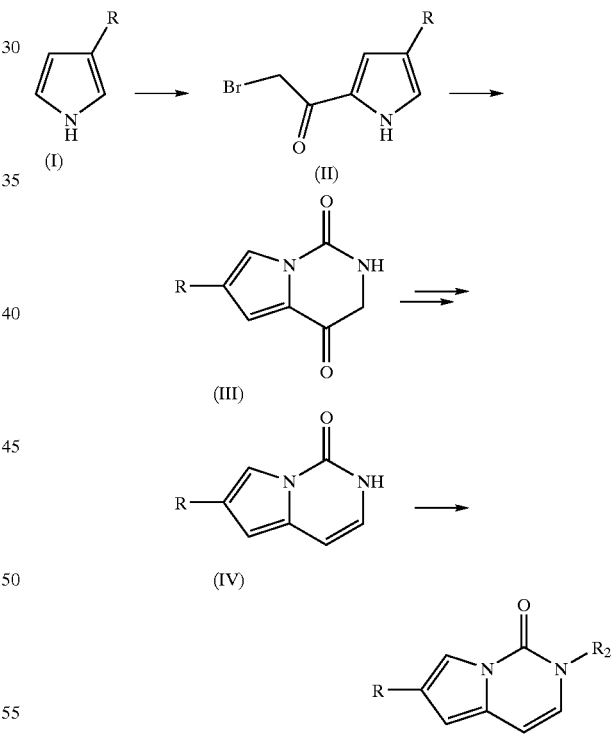

Scheme 1

Scheme 1 represents a method of synthesizing compound of formula (I). Briefly, starting with an appropriately substituted, commercially available pyrrole (Aldrich Chemical Co.), the method of Alvarez et. al (J. Chem. Soc., Perk. Trans I, (3) p249–256, 1999) may be employed to generate this core ring system. Thus, the substituted pyrrole (I) can be acylated to give the bromo ketone (II). Cyclization with cyanate ion would give the bicyclic ketone (III). Reduction of the ketone followed by dehydration would give the desired core ring system (IV). The substituent R can be elaborated to form the appropriate 'linker' and A ring $R^1$ and the NH of the ring can be alkylated to install the other group $R^2$ as defined above.

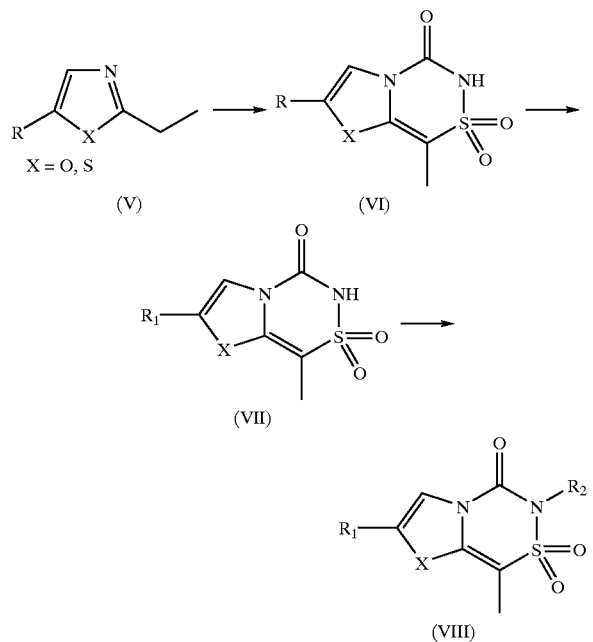

Alternatively, using an appropriately substituted, commercially available oxazole or thiazole (Aldrich Chemical Co.) in the method set forth in Daniel and Dahr (Syn. Comm. 23(1), p121–129, 1993) one can form the desired core ring system which can be further elaborated to give compounds of the present invention. Thus, an oxazole or thiazole (V) can be cyclized with N-chlorosulfonylisocyanate to give the desired core ring (VI). The substituent R can be elaborated to form the appropriate 'linker' and A ring $R^1$ and the NH of the ring can be alkylated to install the other group $R^2$ as defined above.

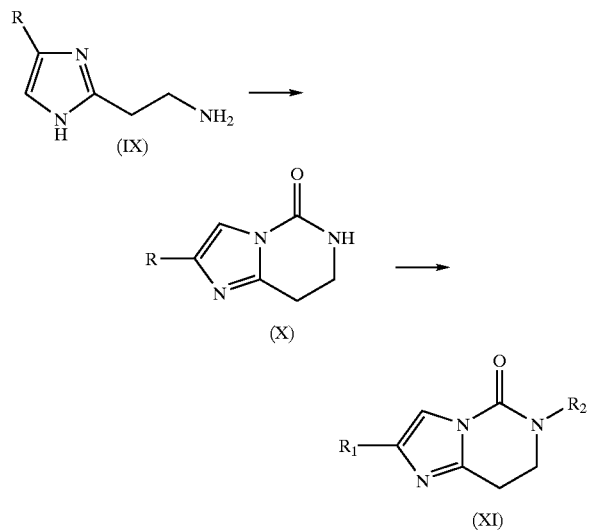

Finally, using an appropriately substituted, commercially available imidazole (Aldrich Chemical Co.) in the method set forth in Buschauer et al (Chem. Ber. 117, p2597–2614, 1984) one can form the desired core ring system which can be further elaborated to give compounds of the present invention. Thus, an imidazole (IX) can be cyclized with CDI to give the desired core ring (X). The substituent R can be elaborated to form the appropriate 'linker' and A ring $R^1$ and the NH of the ring can be alkylated to install the other group $R^2$ as defined above.

The compounds of the formula (i), which are basic in nature, are capable of forming a wide variety of different salts with various inorganic and organic acids. Although such salts must be pharmaceutically acceptable for administration to animals, it is often desirable in practice to initially isolate a compound of the formula (I) from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [1,1'-methylene-bis-(2-hydroxy-3-naphthoate)]salts.

Those compounds of the formula (I) which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula (I). These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure.

Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Biological Assays

The ability of the compounds of formula (I) or their pharmaceutically acceptable salts (hereinafter also referred to as the compounds of the present invention) to inhibit metalloproteinases or mammalian reprolysins and, consequently, demonstrate their effectiveness for treating diseases characterized by metalloproteinase activity is shown by the following in vitro and in viva assay tests.

MMP Assays

MMP-13 selective inhibitors may be identified by screening the inhibitors of the present invention through the MMP fluorescence assays described below and selecting those agents with MMP-13/MMP-X inhibition $IC_{50}$ ratios of 100 or greater and potency of less than 100 nM, where MMP-X refers to one or more other MMP's.

Non-selective collagenase inhibitors as used herein, unless otherwise mentioned, refer to agents which exhibit less than a 100 fold selectivity for the inhibition of MMP-13 enzyme activity over MMP-X enzyme activity or a potency of more than 100 nM as defined by the $IC_{50}$ results from the MMP-13/MMP-X fluorescence assays described below.

The ability of collagenase inhibitors to inhibit collagenase activity is well known in the art. The degree of inhibition of a particular MMP for several compounds has been well documented in the art and those skilled in the art will know how to normalize different assay results to those assays reported herein. The following assays may be used to identify matrix metalloproteinase inhibitors.

Inhibition of Human Collagenase (MMP-1)

Human recombinant collagenase is activated with trypsin. The amount of trypsin is optimized for each lot of collagenase-1 but a typical reaction uses the following ratio: 5 μg trypsin per 100 μg of collagenase. The trypsin and collagenase are incubated at room temperature for 10 minutes then a five fold excess (50 mg/10 mg trypsin) of soybean trypsin inhibitor is added.

Stock solutions (10 mM) of inhibitors are made up in dimethylsulfoxide and then diluted using the following scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D7–D12 and negative controls (no enzyme, no inhibitors) are set in wells D1–D6.

Collagenase-1 is diluted to 240 ng/ml and 25 □l is then added to appropriate wells of the microfluor plate. Final concentration of collagenase in the assay is 60 ng/ml.

Substrate (DNP-Pro-Cha-Gly-Cys(Me)-His-Ala-Lys (NMA)-NH$_2$) is made as a 5 mM stock in dimethylsulfoxide and then diluted to 20 μM in assay buffer. The assay is initiated by the addition of 50 □l substrate per well of the microfluor plate to give a final concentration of 10 □M.

Fluorescence readings (360 nM excitation, 460 nm emission) are taken at time 0 and then at 20 minute intervals. The assay is conducted at room temperature with a typical assay time of 3 hours Fluorescence versus time is then plotted for both the blank and collagenase containing samples (data from triplicate determinations is averaged). A time point that provides a good signal (at least five fold over the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration versus % control (inhibitor fluorescence divided by fluorescence of collagenase alone× 100). $IC_{50}$'s are determined from the concentration of inhibitor that gives a signal that is 50% of the control.

If $IC_{50}$'s are reported to be less than 0.03 □M then the inhibitors are assayed at concentrations of 0.3 □M, 0.03 □M, and 0.003 □M.

Inhibition of Gelatinase (MMP-2)

Human recombinant 72 kD gelatinase (MMP-2, gelatinase A) is activated for 16–18 hours with 1 mM p-aminophenyl-mercuric acetate (from a freshly prepared 100 mM stock in 0.2 N NaOH) at 4° C., rocking gently.

10 mM dimethylsulfoxide stock solutions of inhibitors are diluted serially in assay buffer (50 mM TRIS, pH 7.5, 200 mM NaCl, 5 mM CaCl$_2$, 20 μM ZnCl$_2$ and 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.34 nM).

A five mM dimethylsulfoxide stock solution of substrate (Mca-Pro-Leu-Gly-Leu-DpaAla-Arg-NH$_2$) is diluted in assay buffer to 20 μM. The assay is initiated by addition of 50 μL of diluted substrate yielding a final assay concentration of 10 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Stromelysin Activity (MMP-3)

Human recombinant stromelysin (MMP-3, stromelysin-1) is activated for 20–22 hours with 2 mM p-aminophenyl-mercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 150 mM NaCl, 10 mM CaCl$_2$ and 0.05% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 200 ng/mL in assay buffer, 25 μL per well is added to appropriate wells of the microplate. Final enzyme concentration in the assay is 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-NH$_2$) is diluted in assay buffer to 6 μM. The assay is initiated by addition of 50 μL of diluted substrate yielding a final assay concentration of 3 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for IC$_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. IC$_{50}$'s are defined as the concentration of inhibitor that gives a signal that is 50% of the positive enzyme control.

Inhibition of Human 92 kD Gelatinase (MMP-9)

Inhibition of 92 kD gelatinase (MMP-9) activity is assayed using the Mca-Pro-Leu-Gly-Leu-Dpa-Ala-Arg-NH$_2$ substrate (10 μM) under similar conditions as described above for the inhibition of human collagenase (MMP-1).

Human recombinant 92 kD gelatinase (MMP-9, gelatinase B) is activated for 2 hours with 1 mM p-aminophenylmercuric acetate (from a freshly prepared 100 mM stock in 0.2 N NaOH) at 37 C.

10 mM dimethylsulfoxide stock solutions of inhibitors are diluted serially in assay buffer (50 mM TRIS, pH 7.5, 200 mM NaCl, 5 mM CaCl$_2$, 20 μM ZnCl$_2$, 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.27 nM).

A five mM dimethylsulfoxide stock solution of substrate (Mca-Pro-Leu-Gly-Leu-Dpa-Ala-Arg-NH$_2$) is diluted in assay buffer to 20 μM. The assay is initiated by addition of 50 μL of diluted substrate yielding a final assay concentration of 10 μM substrate. A 0 time fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for IC$_{50}$ determinations. The 0 time point for each compound at each dilution is subtracted from the latter time point and the data then expressed as percent of enzyme control (inhibitor fluorescence divided by fluorescence of positive enzyme control x 100). Data is plotted as inhibitor concentration versus percent of enzyme control. IC$_{50}$'s are defined as the concentration of inhibitor that gives a signal that is 50% of the positive enzyme control.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 μM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 μM, 3 μM, 0.3 μM, and 0.03 μM.

Substrate (Dnp-Pro-Cha-Gly-Cys(Me)-His-Ala-Lys (NMA)-NH$_2$) is prepared as for inhibition of human collagenase (MMP-1) and 50 □l is added to each well to give a final assay concentration of 10 μM. Fluorescence readings (360 nM excitation; 450 emission) are taken at time 0 and every 5 minutes for 1 hour.

Positive controls consist of enzyme and substrate with no inhibitor and blanks consist of substrate only.

IC$_{50}$'s are determined as per inhibition of human collagenase (MMP-1). If IC$_{50}$'s are reported to be less than 0.03 μM, inhibitors are then assayed at final concentrations of 0.3 μM, 0.03 μM, 0.003 μM and 0.0003 μM.

Collagen Film MMP-13 Assay

Rat type I collagen is radiolabeled with $^{14}$C acetic anhydride (T. E. Cawston and A. J. Barrett, *Anal. Biochem.*, 99, 340–345 (1979)) and used to prepare 96 well plates containing radiolabeled collagen films (Barbara Johnson-Wint, *Anal. Biochem.*, 104, 175–181 (1980)). When a solution containing collagenase is added to the well, the enzyme cleaves the insoluble collagen which unwinds and is thus solubilized. Collagenase activity is directly proportional to the amount of collagen solubilized, determined by the proportion of radioactivity released into the supernatant as measured in a standard scintillation counter. Collagenase inhibitors are, therefore, compounds which reduce the radioactive counts released with respect to the controls with no inhibitor present. One specific embodiment of this assay is described in detail below.

For determining the selectivity of compounds for MMP-13 versus MMP-1 using collagen as a substrate, the following procedure is used. Recombinant human proMMP-13 or proMMP-1 is activated according to the procedures outlined above. The activated MMP-13 or MMP-1 is diluted to 0.6 ug/ml with buffer (50 mM Tris pH 7.5, 150 mM NaCl, 10 mM $CaCl_2$, 1 uM $ZnCl_2$, 0.05% Brij-35, 0.02% sodium azide).

Stock solutions of test compound (10 mM) in dimethylsulfoxide are prepared. Dilutions of the test compounds in the Tris buffer, above, are made to 0.2, 2.0, 20, 200, 2000 and 20000 nM.

100 µl of appropriate drug dilution and 100 µl of diluted enzyme are pipetted into wells of a 96 well plate containing collagen films labeled with $^{14}C$-collagen. The final enzyme concentration is 0.3 µg/ml while the final drug concentration is 0.1, 1.0, 10, 100, 1000 nM. Each drug concentration and control is analyzed in triplicate. Triplicate controls are also run for the conditions in which no enzyme is present and for enzyme in the absence of any compound.

The plates are incubated at 37° C. for a time period such that around 30–50% of the available collagen is solubilized—determined by counting additional control wells at various time points. In most cases around 9 hours of incubation are required. When the assay has progressed sufficiently, the supernatant from each well is removed and counted in a scintillation counter. The background counts (determined by the counts in the wells with no enzyme) are subtracted from each sample and the % release calculated in relation to the wells with enzyme only and no inhibitor. The triplicate values for each point are averaged and the data graphed as percent release versus drug concentration. $IC_{50}$'s are determined from the point at which 50% inhibition of release of radiolabeled collagen is obtained.

To determine the identity of the active collagenases in cartilage conditioned medium, assays were carried out using collagen as a substrate, cartilage conditioned medium containing collagenase activity and inhibitors of varying selectivity. The cartilage conditioned medium was collected during the time at which collagen degradation was occurring and thus is representative of the collagenases responsible for the collagen breakdown. Assays were carried out as outlined above except that instead of using recombinant MMP-13 or recombinant MMP-1, cartilage conditioned medium was the enzyme source.

IL-1 Induced Cartilage Collagen Degradation From Bovine Nasal Cartilage

This assay uses bovine nasal cartilage explants which are commonly used to test the efficacy of various compounds to inhibit either IL-1 induced proteoglycan degradation or IL-1 induced collagen degradation. Bovine nasal cartilage is a tissue that is very similar to articular cartilage, i.e. chondrocytes surrounded by a matrix that is primarily type 11 collagen and aggrecan. The tissue is used because it: (1) is very similar to articular cartilage, (2) is readily available, (3) is relatively homogeneous, and (4) degrades with predictable kinetics after IL-1 stimulation.

Two variations of this assay may beused to assay compounds. Both variations give similar data. The two variations are described below:

Variation 1

Three plugs of bovine nasal cartilage (approximately 2 mm diameter×1.5 mm long) are placed into each well of a 24 well tissue culture plate. One ml of serumless medium is then added to each well. Compounds are prepared as 10 mM stock solutions in DMSO and then diluted appropriately in serumless medium to final concentrations, e.g., 50, 500 and 5000 nM. Each concentration is assayed in triplicate.

Human recombinant IL-1α (5 ng/mL) (IL-1) is added to triplicate control wells and to each well containing drug. Triplicate control wells are also set up in which neither drug nor IL-1 are added. The medium is removed and fresh medium containing IL-1 and the appropriate drug concentrations is added on days 6, 12, 18 and 24 or every 3–4 days if necessary. The media removed at each time point is stored at −20° C. for later analysis. When the cartilage in the IL-1 alone wells has almost completely resorbed (about day 21), the experiment is terminated. The medium, is removed and stored. Aliquots (100 ul) from each well at each time point are pooled, digested with papain and then analyzed for hydroxyproline content. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot.

Variation 2

The experimental set-up is the same as outlined above in Variation 1, until day 12. On day 12, the conditioned medium from each well is removed and frozen. Then one ml of phosphate buffered saline (PBS) containing 0.5 µg/ml trypsin is added to each well and incubation continued for a further 48 hours at 37° C. After 48 hours incubation in trypsin, the PBS solution is removed. Aliquots (50 µl) of the PBS/trypsin solution and the previous two time points (days 6 and 12) are pooled, hydrolyzed and hydroxyproline content determined. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot. In this variation, the time course of the experiment is shortened considerably. The addition of trypsin for 48 hours after 12 days of IL-1 stimulation likely releases any type II collagen that has been damaged by collagenase activity but not yet released from the cartilage matrix. In the absence of IL-1 stimulation, trypsin treatment produces only low background levels of collagen degradation in the cartilage explants.

Inhibition of TNF Production

The ability or inability of the compounds or the pharmaceutically acceptable salts thereof to inhibit the production of TNF is shown by the following in vitro assay:

Human Monocyte Assay

Human mononuclear cells were isolated from anti-coagulated human blood using a one-step Ficoll-hypaque separation technique. The mononuclear cells were washed three times in Hanks balanced salt solution (HBSS) with divalent cations and resuspended to a density of $2×10^6$/ml in HBSS containing 1% BSA. Differential counts determined using the Abbott Cell Dyn 3500 analyzer indicated that monocytes ranged from 17 to 24% of the total cells in these preparations.

180 µl of the cell suspension was aliquoted into flat bottom 96 well plates (Costar). Additions of compounds and LPS (100 ng/ml final concentration) gave a final volume of 200 µl. All conditions were performed in triplicate. After a four hour incubation at 37° C. in an humidified $CO_2$ incubator, plates were removed and centrifuged (10 minutes at approximately 250×g) and the supernatants removed and assayed for TNF a using the R&D ELISA Kit.

Aggrecanase Assay

Primary porcine chondrocytes from articular joint cartilage are isolated by sequential trypsin and collagenase digestion followed by collagenase digestion overnight and are plated at $2\times10^5$ cells per well into 48 well plates with 5 $\mu$Ci/ml $^{35}$S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1% PSF/G. The final wash is allowed to sit on the plates in the incubator while making dilutions.

Media and dilutions may be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 Um stock of each compound in DMEM in 96 well plate. Store in freezer overnight. The next day perform serial dilutions in DMEM with IL-1 to 5 uM, 500 nM, and 50 nM. Aspirate final wash from wells and add 50 ul of compound from above dilutions to 450 ul of IL-1 media in appropriate wells of the 48 well plates. Final compound concentrations equal 500 nM, 50 nM, and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 ul) followed by compound (50 ul) so as to initiate the assay. Plates are incubated at 37° C., with a 5% $CO_2$ atmosphere.

At 40–50% release (when CPM from IL-1 media is 4–5 times control media) as assessed by liquid scintillation counting (LSC) of media samples, the assay is terminated (912 hours). Media is removed from all wells and placed in scintillation tubes. Scintillate is added and radioactive counts are acquired (LSC). To solubilize cell layers, 500 ul of papain digestion buffer (0.2 M Tris, pH 7.0, 5 mM EDTA, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

Thiopeptolide Assay

Thiopeptolide substrates show virtually no decomposition or hydrolysis at or below neutral pH in the absence of a matrix metalloproteinase enzyme. A typical thiopeptolide substrate commonly utilized for assays is Ac-Pro-Leu-Gly-thioester-Leu-Leu-Gly-OEt. A 100 $\mu$L assay mixture will contain 50 mM of N-2-hydroxyethylpiperazine-N'-2-ethanesulfonic acid buffer ("HEPES," pH 7.0), 10 mM $CaCl_2$, 100 $\mu$M thiopeptolide substrate, and 1 mM 5,5'-dithio-bis-(2-nitro-benzoic acid) (DTNB). The thiopeptolide substrate concentration may be varied, for example from 10 to 800 $\mu$M to obtain $K_m$ and $K_{cat}$ values. The change in absorbance at 405 nm is monitored on a Thermo Max microplate reader (molecular Devices, Menlo Park, Calif.) at room temperature (22° C.). The calculation of the amount of hydrolysis of the thiopeptolide substrate is based on $E_{412}$= 13600 $M^{-1}$ $cm^{-1}$ for the DTNB-derived product 3-carboxy-4-nitrothiophenoxide. Assays are carried out with and without matrix metalloproteinase inhibitor compounds, and the amount of hydrolysis is compared for a determination of inhibitory activity of the test compounds.

Test compounds are evaluated at various concentrations in order to determine their respective $IC_{50}$ values, the micromolar concentration of compound required to cause a 50% inhibition of catalytic activity of the respective enzyme.

It should be appreciated that the assay buffer used with MMP-3CD was 50 mM N-morpholinoethane sulfonate ("MES") at pH 6.0 rather than the HEPES buffer at pH 7.0 described above.

The test described above for the inhibition of MMP-13 may also be adapted and used to determine the ability of the compounds of Formula (I) to inhibit the matrix metalloproteases MMP-1, MMP-2, MMP-3, MMP-7, MMP-9, MMP-12 and MMP-14.

MMP-13 Inhibition Assay

Some representative compounds of Formula (I) may beevaluated for their ability to inhibit MMP-13. Inhibitor activity versus other MMPs with the compounds may be determined using, for example, MMP-1FL, which refers to full length interstitial collagenase; MMP-2FL, which refers to full length Gelatinase A; MMP-3CD, which refers to the catalytic domain of stromelysin; MMP-7FL, which refers to full length matrilysin; MMP-9FL, which refers to full length Gelatinase B; MMP-13CD, which refers to the catalytic domain of collagenase 3; and MMP-14CD, which refers to the catalytic domain of MMP-14. Test compounds may be evaluated at various concentrations in order to determine their respective $IC_{50}$ values, the micromolar concentration of compound required to cause a 50% inhibition of the hydrolytic activity of the respective enzyme.

The results of the above assays with other MMPs establishes that the compounds of Formula (I) are potent inhibitors of MMP enzymes, and are especially useful due to their selective inhibition of MMP-13. Because of this potent and selective inhibitory activity, the compounds are especially useful to treat diseases mediated by the MMP enzymes.

Allosteric inhibitors of MMP-13 which are compounds of Formula (I) may be readily identified by assaying a test compound for inhibition of MMP-13 according to the methods described below.

Fluorigenic Peptide-1 Substrate Based Assay

Fluorigenic peptide-1 substrate based assay for identifying compounds of Formula (I) as allosteric inhibitors of MMP-13:

Final assay conditions:
50 mM HEPES buffer (pH 7.0)
10 mM $CaCl_2$
10 $\mu$M fluorigenic peptide-1 ("FP1") substrate 0 or 15 mM acetohydroxamic acid (AcNHOH)=1 $K_d$ 2% DMSO (with or without inhibitor test compound)

0.5 nM MMP-13CD enzyme

Stock solutions:
1) 10× assay buffer: 500 mM HEPES buffer (pH 7.0) plus 100 mM $CaCl_2$
2) 10 mM FP1 substrate: (Mca)-Pro-Leu-Gly-Leu-(Dnp)-Dpa-Ala-Arg-$NH_2$ (Bachem, M-1895; "A novel coumarin-labeled peptide for sensitive continuous assays of the matrix metalloproteinases," Knight C. G., Willenbrock F., and Murphy, G., FEBS Lett., 1992;296:263–266). Is prepared 10 mM stock by dissolving 5 mg FP1 in 0.457 mL DMSO.
3) 3 M AcNHOH: Is prepared by adding 4 mL $H_2O$ and 1 mL 10× assay buffer to 2.25 g AcNHOH (Aldrich 15,903–4). Adjusting pH to 7.0 with NaOH. Diluting volume to 10 mL with $H_2O$. Final solution will contain 3 M AcNHOH, 50 mM HEPES buffer (pH 7.0), and 10 mM $CaCl_2$.
4) AcNHOH dilution buffer: 50 mM HEPES buffer (pH 7.0) plus 10 mM $CaCl_2$
5) MMP-13CD enzyme: Stock concentration=250 nM.
6) Enzyme dilution buffer: 50 mM HEPES buffer (pH 7.0), 10 mM $CaCl_2$, and 0.005% BRIJ 35 detergent (Calbiochem 203728; Protein Grade, 10%)

Procedure (for one 96-well microplate):

A. Prepared assay mixture:

1100 µL 10× assay buffer

11 µL 10 mMFP1

55 µL 3 M AcNHOH or 55 µL AcNHOH dilution buffer

8500 µL $H_2O$

B. Diluted MMP-13CD to 5 nM working stock:

22 µL MMP-13CD (250 nM)

1078 µL enzyme dilution buffer

C. Ran kinetic assay:
1. Dispense 2 µL inhibitor test sample (in 100% DMSO) into well.
2. Add 88 µL assay mixture and mix well, avoiding bubbles.
3. Initiate reactions with 10 µL of 5 nM MMP-13CD; mix well, avoid bubbles.
4. Immediately measure the kinetics of the reactions at room temperature.

Fluorimeter: $F_{max}$ Fluorescence Microplate Reader & SOFTMAX PRO Version 1.1 software (Molecular Devices Corporation; Sunnyvale, Calif. 94089).

| Protocol menu: | |
|---|---|
| excitation: 320 nm | emission: 405 nm |
| run time: 15 mm | interval: 29 sec |
| RFU mm: −10 | RFU max: 200 |
| $V_{max}$ points: 32/32 | |

D. Compared % of control activity and/or $IC_{50}$ with inhibitor test compound ±AcNHOH.

Hydrolysis of the fluorigenic peptide-1 substrate, [(Mca) Pro-Leu-Gly-Leu-Dpa-Ala-Arg-$NH_2$; Bachem, catalog number M-1895], wherein "Mca" is (7-methoxy-coumarin-4-yl)acetyl and "Dpa" is (3-[2,4-dinitrophenyl]-L-2,3-diaminopropionyl), is used to screen for MMP-13 catalytic domain (CD) inhibitors. (Dpa may also be abbreviated as "Dnp".) Reactions (100 µL) contain 0.05 M Hepes buffer (pH 7), 0.01 M calcium chloride, 0.005% polyoxyethylene (23) lauryl ether ("Brij 35"), 0 or 15 mM acetohydroxamic acid, 10 µM FP1, and 0.1 mM to 0.5 nM inhibitor in DMSO (2% final).

After recombinant human MMP-13CD (0.5 nM final) is added to initiate the reaction, the initial velocity of FP1 hydrolysis is determined by monitoring the increase in fluorescence at 405 nm (upon excitation at 320 nm) continuously for up to 30 minutes on a microplate reader at room temperature. Alternatively, an endpoint read can also be used to determine reaction velocity provided the initial fluorescence of the solution, as recorded before addition of enzyme, is subtracted from the final fluorescence of the reaction mixture. The inhibitor is assayed at different concentration values, such as, for example, 100 µM, 10 µM, 1 µM, 100 nM, 10 nM, and 1 nM. Then the inhibitor concentration is plotted on the X-axis against the percentage of control activity observed for inhibited experiments versus uninhibited experiments (i.e., (velocity with inhibitor) divided by (velocity without inhibitor)×100) on the Y-axis to determine $IC_{50}$ values. This determination is done for experiments done in the presence, and experiments done in the absence, of acetohydroxamic acid. Data are fit to the equation: percent control activity=$100/[1+(([I]/IC_{50})^{slope})]$, where [I] is the inhibitor concentration, $IC_{50}$ is the concentration of inhibitor where the reaction rate is 50% inhibited relative to the control, and slope is the slope of the $IC_{50}$ curve at the curve's inflection point, using nonlinear least-squares curve-fitting equation regression.

Results may be expressed as an $IC_{50}$ Ratio (+/−) ratio, which means a ratio of the $IC_{50}$ of the inhibitor with MMP-13 and an inhibitor to the catalytic zinc of MMP-13, divided by the $IC_{50}$ of the inhibitor with MMP-13 without the inhibitor to the catalytic zinc of MMP-13. Compounds of Formula (I) which are allosteric inhibitors of MMP-13 are expected to have an $IC_{50}$ Ratio (+/−) ratio of less than 1, and are expected to be synergistic with the inhibitor to the catalytic zinc of MMP-13 such as, for example, AcNHOH. Compounds of Formula (I)—III which are not allosteric inhibitors of MMP-13 will be inactive in the assay or will have an $IC_{50}$ Ratio (+/−) of greater than 1, unless otherwise indicated. Results may be confirmed by kinetics experiments that are well known in the biochemical art.

Fluorigenic Peptide-1 Based Assay

Fluorigenic peptide-1 based assay for identifying allosteric alkyne inhibitors of matrix metalloproteinase-13 catalytic domain ("MMP-13CD"):

In a manner similar to immediately above, an assay is run wherein 1,10-phenanthroline is substituted for acetohydroxamic acid to identify compounds of Formula (I)CD.

Animal models may be used to establish that the instant compounds of Formula (I), or a pharmaceutically acceptable salt thereof, would be useful for preventing, treating, and inhibiting cartilage damage, and thus for treating osteoarthritis, for example. Examples of such animal models are described below.

Monosodium Iodoacetate-Induced Osteoarthritis in Rat Model of Cartilage Damage ("MIA Rat")

One end result of the induction of osteoarthritis in this model, as determined by histologic analysis, is the development of an osteoarthritic condition within the affected joint, as characterized by the loss of Toluidine blue staining and formation of osteophytes. Associated with the histologic changes is a concentration-dependent degradation of joint cartilage, as evidenced by affects on hind-paw weight distribution of the limb containing the affected joint, the presence of increased amounts of proteoglycan or hydroxyproline in the joint upon biochemical analysis, or histopathological analysis of the osteoarthritic lesions.

Generally, In the MIA Rat model on Day 0, the hind-paw weight differential between the right arthritic joint and the left healthy joint of male Wistar rats (150 g) are determined with an incapacitance tester, model 2KG (Linton Instrumentation, Norfolk, United Kingdom). The incapacitance tester has a chamber on top with an outwardly sloping front wall that supports a rat's front limbs, and two weight sensing pads, one for each hind paw, that facilitates this determination. Then the rats are anesthetized with isofluorine, and the right, hind leg knee joint is injected with 1.0 mg of mono-iodoacetate ("MIA") through the infrapatellar ligament. Injection of MIA into the joint results in the inhibition of glycolysis and eventual death of surrounding chondrocytes. The rats are further administered either an invention compound or vehicle (in the instant case, water) daily for 14 days or 28 days. The invention compound is typically administered at a dose of 30 mg per kilogram of rat per day (30 mg/kg/day), but the invention compound may be administered at other doses such as, for example, 10 mg/kg/day, 60 mg/kg/day, 90-mg/kg/day, or 100 mg/kg/day according to the requirements of the compound being studied. It is well within the level of ordinary skill in the pharmaceutical arts to determine a proper dosage of an invention compound in this model. Administration of the invention compound in this model is optionally by oral administration or intravenous administration via an osmotic pump. After 7 and 14 days for a two-week study, or 7, 14, and 28 days for a four-week study, the hind-paw weight distribution is again determined. Typically, the animals administered vehicle alone place greater weight on their unaffected left hind paw than on their right hind paw, while animals administered an invention compound show a more normal (i.e., more like a healthy animal) weight distribution between their hind paws. This change in weight distribution was proportional to the degree of joint cartilage damage. Percent inhibition of a change in hind paw joint function is calculated as the percent change in hind-paw weight distribution for treated animals versus control animals. For example, for a two week study, Percent inhibition of a change in hind paw weight distribution =

$$\left\{1 - \left[\frac{(\Delta W_G)}{(\Delta W_C)}\right]\right\} \times 100$$

wherein:

$\Delta W_C$ is the hind-paw weight differential between the healthy left limb and the arthritic limb of the control animal administered vehicle alone, as measured on Day 14; and $\Delta W_G$ is the hind-paw weight differential between the healthy left limb and the arthritic limb of the animal administered an invention compound, as measured on Day 14.

In order to measure biochemical or histopathological end points in the MIA Rat model, some of the animals in the above study may be sacrificed, and the amounts of free proteoglycan in both the osteoarthritic right knee joint and the contralateral left knee joint may be determined by biochemical analysis. The amount of free proteoglycan in the contralateral left knee joint provides a baseline value for the amount of free proteoglycan in a healthy joint. The amount of proteoglycan in the osteoarthritic right knee joint in animals administered an invention compound, and the amount of proteoglycan in the osteoarthritic right knee joint in animals administered vehicle alone, are independently compared to the amount of proteoglycan in the contralateral left knee joint. The amounts of proteoglycan lost in the osteoarthritic right knee joints are expressed as percent loss of proteoglycan compared to the contralateral left knee joint control. The percent inhibition of proteoglycan loss, may be calculated as {[(proteoglycan loss from joint (%) with vehicle)−(proteoglycan loss from joint with an invention compound)]÷(proteoglycan loss from joint (%) with vehicle)}×100.

The MIA Rat data that are expected from the analysis of proteoglycan loss would establish that an invention compound is effective for inhibiting cartilage damage and inflammation and/or alleviating pain in mammalian patients, including human.

The results of these studies with oral dosing may be presented in tabular format in the columns labelled "IJFL (%+/− SEM)", wherein IJFL means Inhibition of Joint Function Limitation, "SDCES", wherein SDCES means Significant Decrease In Cartilage Erosion Severity, and "SIJWHLE", wherein SIJWHLE means Significant Increase in Joints Without Hind Limb Erosion.

The proportion of subjects without hind limb erosions may be analyzed via an *Exact Sequential Cochran-Armitage Trend* test (SAS® Institute, 1999). The Cochran-Armitage Trend test is employed when one wishes to determine whether the proportion of positive or "Yes" responders increases or decreases with increasing levels of treatment. For the particular study, it is expected that the number of animals without joint erosions increased with increasing dose.

The ridit analysis may be used to determine differences in overall erosion severity. This parameter takes into account both the erosion grade (0=no erosion, I=erosion extending into the superficial or middle layers, or II=deep layer erosion), and area (small, medium and large, quantified by dividing the area of the largest erosion in each score into thirds) simultaneously. The analysis recognizes that each unit of severity is different, but does not assume a mathematical relationship between units.

Another animal model for measuring effects of an invention compound on cartilage damage and inflammation and/or pain is described below in Biological Method 6.

Induction of Experimental Osteoarthritis in Rabbit ("EOA in Rabbit")

Normal rabbits are anaesthetized and anteromedial incisions of the right knees performed. The anterior cruciate ligaments are visualized and sectioned. The wounds are closed and the animals are housed in individual cages, exercised, and fed ad libitum. Rabbits are given either vehicle (water) or an invention compound dosed three times per day with 30-mg/kg/dose or 10-mg/kg/dose. The invention compound may be administered at other doses such as, for example, 3 times 20 mg/kg/day or 3 times 60 mg/kg/day according to the requirements of the invention compound being studied. The rabbits are euthanized 8 weeks after surgery and the proximal end of the tibia and the distal end of the femur are removed from each animal.

Macroscopic Grading

The cartilage changes on the femoral condyles and tibial plateaus are graded separately under a dissecting microscope (Stereozoom, Bausch & Lomb, Rochester, N.Y.). The depth of erosion is graded on a scale of 0 to 4 as follows: grade 0=normal surface; Grade 1=minimal fibrillation or a slight yellowish discoloration of the surface; Grade 2=erosion extending into superficial or middle layers only; Grade 3=erosion extending into deep layers; Grade 4=erosion extending to subchondral bone. The surface area changes are measured and expressed in mm$^2$. Representative specimens may also be used for histologic grading (see below).

Histologic Grading

Histologic evaluation is performed on sagittal sections of cartilage from the lesional areas of the femoral condyle and tibial plateau. Serial sections (5 um) are prepared and stained with safranin-O. The severity of OA lesions is graded on a scale of 0–14 by two independent observers using the histologic-histochemical scale of Mankin et al This scale evaluates the severity of OA lesions based on the loss of safranin-O staining (scale 0–4), cellular changes (scale 0–3), invasion of tidemark by blood vessels (scale 0–1) and structural changes (scale 0–6). On this latter scale, 0 indicates normal cartilage structure and 6 indicates erosion of the cartilage down to the subchondral bone. The scoring system is based on the most severe histologic changes in the multiple sections.

Representative specimens of synovial membrane from the medial and lateral knee compartments are dissected from underlying tissues. The specimens are fixed, embedded, and sectioned (5 um) as above, and stained with hematoxylin-eosin. For each compartment, two synovial membrane specimens are examined for scoring purposes and the highest score from each compartment is retained. The average score is calculated and considered as a unit for the whole knee. The severity of synovitis is graded on a scale of 0 to 10 by two independent observers, adding the scores of 3 histologic criteria: synovial lining cell hyperplasia (scale 0–2); villous hyperplasia (scale 0–3); and degree of cellular infiltration by mononuclear and polymorphonuclear cells (scale 0–5): 0 indicates normal structure.

Statistical Analysis

Mean values and SEM is calculated and statistical analysis was done using the Mann-Whitney U-test.

The results of these studies would be expected to show that an invention compound would reduce the size of the lesion on the tibial plateaus, and perhaps the damage in the tibia or on the femoral condyles. In conclusion, these results would show that an invention compound would have significant inhibition effects on the damage to cartilage.

The foregoing studies establish that an invention compound is effective for the inhibition of cartilage damage and inflammation and/or alleviating pain, and thus useful for the treatment of osteoarthritis or rheumatoid arthritis in human, and other mammalian disorders. Such a treatment offers a distinct advantage over existing treatments that only modify pain or inflammation or and other secondary symptoms. The effectiveness of an invention compound in this model would indicate that the invention compound will have clinically useful effects in preventing and/or treating cartilage damage, pain and/or inflammation.

Administration according to the invention method of an invention compound to a mammal to treat the diseases listed above is preferably, although not necessarily, accomplished by administering the compound, or a salt thereof, in a pharmaceutical dosage form.

The compounds of Formula (I), or a pharmaceutically acceptable salt thereof, may be prepared and administered according to the invention method in a wide variety of oral and parenteral pharmaceutical dosage forms. Thus, the compounds of Formula (I), or a pharmaceutically acceptable salt thereof, may be administered by injection, that is, intravenously, intramuscularly, intracutaneously, subcutaneously, intraduodenally, or intraperitoneally. Also, the compounds of Formula (I), or a pharmaceutically acceptable salt thereof, may be administered by inhalation, for example, intranasally. Additionally, the compounds of Formula (I), or a pharmaceutically acceptable salt thereof, may be administered transdermally. It will be obvious to those skilled in the art that the following dosage forms may comprise as the active component an invention compound. The invention compounds generally are present in a concentration of about 5% to about 95% by weight of the formulation.

In so far as the compositions of the present invention contain an "effective amount" of a compound of the present invention, the term "effective amount" refers to that amount sufficient to inhibit, halt, or cause regression of the disorder for which it is being administered. For example, if a compound of the invention is administered to treat a patient suffering from arthritis, it will be administered in an anti-arthritic effective amount, i.e., that amount which is sufficient to inhibit, halt or cause the regression of arthritis in a patient. Similarly, if a compound of the invention is administered to treat a patient suffering from osteoarthritis or rheumatoid arthritis, it will be administered in an amount that is effective to inhibit, halt or cause the regression of osteoarthritis or rheumatoid arthritis, respectively, in a patient. In humans or other mammals, an effective amount of a compound for the treatment of a given disorder may be determined experimentally in a laboratory or clinical setting, or may be the amount required by the guidelines of the United States Food and Drug Administration, or equivalent foreign agency, for the particular disorder and patient being treated, taking into account the patient's age, weight, gender, and medical conditions, as well as the route of administration of the compound.

For preparing pharmaceutical compositions from the compounds of Formula (I), or a pharmaceutically acceptable salt thereof, (i.e., the active component) pharmaceutically acceptable carriers may be either solid or liquid. Solid form preparations are preferred. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component. Powders suitable for intravenous administration or administration by injection may be lyophilized.

In tablets, the active component is mixed with the carrier having the necessary binding properties in suitable proportions and compacted in the shape and size desired.

The powders and tablets preferably contain from about 5% to about 70%, total, of the active component. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active component with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges may be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations may be formulated in solution in aqueous polyethylene glycol solution.

Aqueous solutions suitable for oral use may be prepared by dissolving the active component in water and adding suitable colorants, flavors, stabilizing, and thickening agents as desired.

Aqueous suspensions suitable for oral use may be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing an appropriate quantity of the active component. The unit dosage form may be a packaged preparation, the package containing discrete quantities of preparation, such as packeted tablets, capsules, and powders in vials or ampoules. Also, the unit dosage form may be a capsule, tablet, cachet, or lozenge itself, or it may be the appropriate number of any of these in packaged form.

The quantity of active component in a unit dose preparation may be varied or adjusted from 0.01 to 1000 mg, preferably 1 to 500 mg according to the particular application and the potency of the active components. The composition can, if desired, also contain other compatible therapeutic agents.

In therapeutic use as agents to treat the above-listed diseases, the compounds of Formula (I), or a pharmaceutically acceptable salt thereof, are administered at a dose that is effective for treating at least one symptom of the disease or disorder being treated. The initial dosage of about 1 mg/kg to about 100 mg/kg daily of the active component will be effective. A daily dose range of about 25 mg/kg to about 75 mg/kg of the active component is preferred. The dosages, however, may be varied depending upon the requirements of the patient, the severity of the condition being treated, and the particular invention compound being employed in the invention combination. Determination of the proper dosage for a particular situation is within the skill of the art as described above. Typical dosages will be from about 0.1 mg/kg to about 500 mg/kg, and ideally about 25 mg/kg to about 250 mg/kg, such that it will be an amount that is effective to treat the particular disease or disorder being treated.

A preferred composition for dogs comprises an ingestible liquid peroral dosage form selected from the group consisting of a solution, suspension, emulsion, inverse emulsion, elixir, extract, tincture and concentrate, optionally to be added to the drinking water of the dog being treated. Any of these liquid dosage forms, when formulated in accordance with methods well known in the art, can either be administered directly to the dog being treated, or may be added to the drinking water of the dog being treated. The concentrate liquid form, on the other hand, is formulated to be added first to a given amount of water, from which an aliquot amount may be withdrawn for administration directly to the dog or addition to the drinking water of the dog.

A preferred composition provides delayed-, sustained- and/or controlled-release of an invention compound. Such preferred compositions include all such dosage forms which produce $\geq 40\%$ inhibition of cartilage degradation, and result in a plasma concentration of the active component of at least 3 fold the active component's $ED_{40}$ for at least 2 hours; preferably for at least 4 hours; preferably for at least 8 hours; more preferably for at least 12 hours; more preferably still for at least 16 hours; even more preferably still for at least 20 hours; and most preferably for at least 24 hours. Preferably, there is included within the above-described dosage forms those which produce $\geq 40\%$ inhibition of cartilage degradation, and result in a plasma concentration of the active component of at least 5 fold the active component's $ED_{40}$ for at least 2 hours, preferably for at least 2 hours, preferably for at least 8 hours, more preferably for at least 12 hours, still more preferably for at least 20 hours and most preferably for at least 24 hours. More preferably, there is included the above-described dosage forms which produce $\geq 50\%$ inhibition of cartilage degradation, and result in a plasma concentration of the active component of at least 5 fold the active component's $ED_{40}$ for at least 2 hours, preferably for at least 4 hours, preferably for at least 8 hours, more preferably for at least 12 hours, still more preferably for at least 20 hours and most preferably for at least 24 hours.

The following Formulation Examples 1 to 8 illustrate the invention pharmaceutical compositions. When the formulations comprise the invention compound and a pharmaceutically acceptable carrier, diluent, or excipient, they contain a cartilage damage treating effective amount or a therapeutically effective amount such as, for example, an antiosteoarthritic effective amount of the invention compound. The examples are representative only, and are not to be construed as limiting the invention in any respect.

FORMULATION EXAMPLE 1

| Tablet Formulation: | |
|---|---|
| Ingredient | Amount (mg) |
| An invention compound | 25 |
| Lactose | 50 |
| Cornstarch (for mix) | 10 |
| Cornstarch (paste) | 10 |
| Magnesium stearate (1%) | 5 |
| Total | 100 |

The invention compound, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets may be administered to a human from one to four times a day for inhibiting cartilage damage or treating osteoarthritis.

FORMULATION EXAMPLE 2

Coated Tablets:

The tablets of Formulation Example 1 are coated in a customary manner with a coating of sucrose, potato starch, talc, tragacanth, and colorant.

FORMULATION EXAMPLE 3

Injection Vials:

The pH of a solution of 500 g of an invention compound and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 25 mg of the invention compound.

FORMULATION EXAMPLE 4

Suppositories:

A mixture of 25 g of an invention compound, 100 g of soya lecithin, and 1400 g of cocoa butter is fused, poured into molds, and allowed to cool. Each suppository contains 25 mg of the invention compound.

FORMULATION EXAMPLE 5

Solution:

A solution is prepared from 1 g of an invention compound, 9.38 g of $NaH_2PO_4.12H_2O$, 28.48 g of $Na_2HPO_4.12H_2O$, and 0.1 g benzalkonium chloride in 940 mL of double-distilled water. The pH of the solution is adjusted to pH 6.8 using 2 M hydrochloric acid. The solution is diluted to 1.0 L with double-distilled water, and sterilized by irradiation. A 25 mL volume of the solution contains 25 mg of the invention compound.

FORMULATION EXAMPLE 6

Ointment:

500 mg of an invention compound is mixed with 99.5 g of petroleum jelly under aseptic conditions. A 5 g portion of the ointment contains 25 mg of the invention compound.

FORMULATION EXAMPLE 7

Capsules:

2 kg of an invention compound are filled into hard gelatin capsules in a customary manner such that each capsule contains 25 mg of the invention compound.

FORMULATION EXAMPLE 8

Ampoules:

A solution of 2.5 kg of an invention compound is dissolved in 60 L of double-distilled water. The solution is sterile filtered, and the filtrate is filled into ampoules. The ampoules are lyophilized under sterile conditions and aseptically sealed. Each ampoule contains 25 mg of the invention compound.

The following Formulation Examples 9 to 16 illustrate the invention pharmaceutical compositions containing an invention combination in a single formulation with a pharmaceutically acceptable carrier, diluent, or excipient. The examples are representative only, and are not to be construed as limiting the invention in any respect.

FORMULATION EXAMPLE 9

| Tablet Formulation: | |
|---|---|
| Ingredient | Amount (mg) |
| An invention compound | 25 |
| A COX-2 inhibitor | 20 |
| Lactose | 50 |
| Cornstarch (for mix) | 10 |
| Cornstarch (paste) | 10 |
| Magnesium stearate (1%) | 5 |
| Total | 120 |

The invention compound or COX-2 inhibitor, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets may be administered to a human from one to four times a day for treatment of one of the above-listed diseases.

FORMULATION EXAMPLE 10

Coated Tablets:

The tablets of Formulation Example 9 are coated in a customary manner with a coating of sucrose, potato starch, talc, tragacanth, and colorant.

FORMULATION EXAMPLE 11

Injection Vials:

The pH of a solution of 250 g of a COX-2 inhibitor, 500 g of an invention compound, and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 12.5 mg of COX-2 inhibitor and 25 mg of the invention compound.

FORMULATION EXAMPLE 12

Suppositories:

A mixture of 50 g of a COX-2 inhibitor, 25 g of an invention compound, 100 g of soya lecithin, and 1400 g of cocoa butter is fused, poured into molds, and allowed to cool. Each suppository contains 50 mg of the COX-2 inhibitor and 25 mg of the invention compound.

FORMULATION EXAMPLE 13

Solution:

A solution is prepared from 0.5 g of a COX-2 inhibitor, 1 g of an invention compound, 9.38 g of $NaH_2PO_4.12H_2O$, 28.48 g of $Na_2HPO_4.12H_2O$, and 0.1 g benzalkonium chloride in 940 mL of double-distilled water. The pH of the solution is adjusted to pH 6.8 using 2 M hydrochloric acid. The solution is diluted to 1.0 L with double-distilled water, and sterilized by irradiation. A 25 mL volume of the solution contains 12.5 mg of the COX-2 inhibitor and 25 mg of the invention compound.

FORMULATION EXAMPLE 14

Ointment:

100 mg of a COX-2 inhibitor, 500 mg of an invention compound is mixed with 99.4 g of petroleum jelly under aseptic conditions. A 5 g portion of the ointment contains 5 mg of the COX-2 inhibitor and 25 mg of the invention compound.

FORMULATION EXAMPLE 15

Capsules:

2 kg of a COX-2 inhibitor and 20 kg of an invention compound are filled into hard gelatin capsules in a customary manner such that each capsule contains 25 mg of the COX-2 inhibitor and 250 mg of the invention compound.

FORMULATION EXAMPLE 16

Ampoules:

A solution of 2.5 kg of a COX-2 inhibitor and 2.5 kg of an invention compound is dissolved in 60 L of double-distilled water. The solution is sterile filtered, and the filtrate is filled into ampoules. The ampoules are lyophilized under sterile conditions and aseptically sealed. Each ampoule contains 25 mg each of the COX-2 inhibitor and the invention compound.

While it may be desirable to formulate a COX-2 inhibitor and an invention compound together in one capsule, tablet, ampoule, solution, and the like, for simultaneous administration, it is not necessary for the purposes of practicing the invention methods. A COX-2 inhibitor and an invention compound alternatively can each be formulated independently in any form such as, for example, those of any one Formulation Examples 1 to 16, and administered to a patient either simultaneously or at different times.

The following examples illustrate the invention pharmaceutical compositions containing discrete formulations of the active components of an invention combination and a pharmaceutically acceptable carrier, diluent, or excipient. The examples are representative only, and are not to be construed as limiting the invention in any respect.

FORMULATION EXAMPLE 17

Tablet Formulation of an invention compound:

| Ingredient | Amount (mg) |
| --- | --- |
| An invention compound | 25 |
| Lactose | 50 |
| Cornstarch (for mix) | 10 |
| Cornstarch (paste) | 10 |
| Magnesium stearate (1%) | 5 |
| Total | 100 |

An invention compound, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet.

Injection Vial Formulation of a COX-2 Inhibitor:

The pH of a solution of 500 g of a COX-2 inhibitor and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 25 mg of the COX-2 inhibitor.

Such tablets containing the invention compound may be administered to a human from one to four times a day for treatment of the above-listed diseases, and the injection solutions containing the COX-2 inhibitor may be administered to a human 1 or 2 times per day, wherein the administration by injection is optionally simultaneous with administration of the tablets or at different times, for the treatment of one of the above-listed diseases.

FORMULATION EXAMPLE 18

Coated Tablets containing an invention compound:

The tablets of Formulation Example 17 are coated in a customary manner with a coating of sucrose, potato starch, talc, tragacanth, and colorant.

Capsules containing valdecoxib or celecoxib:

2 kg of a COX-2 inhibitor are filled into hard gelatin capsules in a customary manner such that each capsule contains 25 mg of the COX-2 inhibitor.

Such coated tablets containing the invention compound may be administered to a human from one to four times a day for treatment of the above-listed diseases, and the capsules containing the COX-2 inhibitor may be administered to a human 1 or 2 times per day, wherein the administration of the capsules is optionally simultaneous with administration of the tablets or at different times, for the treatment of one of the above-listed diseases.

Still further, it should be appreciated that the invention methods comprising administering an invention combination to a mammal to treat diseases or disorders listed above may be used to treat different diseases simultaneously. For example, administration of a COX-2 inhibitor in accordance with the invention combination may be carried out as described above to treat inflammation, arthritic pain, pain associated with menstrual cramping, and migraines, while an invention compound may be administered to treat OA or inhibit cartilage damage.

As shown above, the invention methods comprising administering an invention compound offer a distinct advantage over existing treatments for diseases such as OA that comprise cartilage damage, wherein the existing treatments modify pain or secondary symptoms, but do not show a disease modifying effect.

The compounds of the present invention that were tested all have $IC_{50}$'s in at least one of the above assays of less than 100 $\mu M$ preferably less than 100 nM. Certain preferred groups of compounds possess differential selectivity toward the various MMP's or ADAMs. One group of preferred compounds possess selective activity towards MMP-13 over MMP-1. Another preferred group of compounds possess selective activity towards MMP-13 over MMP1 and MMP-12.

For administration to mammals, including humans, for the inhibition of matrix metalloproteinases or mammalian reprolysin, a variety of conventional routes may be used including oral, parenteral (e.g., intravenous, intramuscular or subcutaneous), buccal, anal and topical. In general, the compounds of the invention (hereinafter also known as the active compounds) will be administered at dosages between about 0.1 and 25 mg/kg body weight of the subject to be treated per day, preferably from about 0.3 to 5 mg/kg. Preferably the active compound will be administered orally or parenterally. However, some variation in dosage will necessarily occur depending on the condition of the subject being treated. The person responsible for administration will, in any event, determine the appropriate dose for the individual subject.

The compounds of the present invention may be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds may be administered intramuscularly or subcutaneously at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

For topical ocular administration, direct application to the affected eye may be employed in the form of a formulation as eyedrops, aerosol, gels or ointments, or may be incorporated into collagen (such as poly-2-hydroxyethylmethacrylate and co-polymers thereof, or a hydrophilic polymer shield. The materials can also be applied as a contact lens or via a local reservoir or as a subconjunctival formulation.

For intraorbital administration a sterile injectable solution of the active ingredient is usually prepared. Solutions of a therapeutic compound of the present invention in an aqueous solution or suspension (particle size less than 10 micron) may be employed. The aqueous solutions should be suitably adjusted and buffered, preferably at a pH between 5 and 8, if necessary and the liquid diluent first rendered isotonic. Small amounts of polymers may be added to increase viscosity or for sustained release (such as cellulosic polymers, Dextran, polyethylene glycol, or alginic acid). These solutions are suitable for intraorbital injection purposes. The preparation of all these solutions under sterile conditions is readily accomplished by standard pharmaceutical techniques well known to those skilled in the art. In the case of animals, compounds may be administered intraorbitally at dosage levels of about 0.1 to 50 mg/kg/day, advantageously 0.2 to 10 mg/kg/day given in a single dose or up to 3 divided doses.

As with the other routes of administration and corresponding dosage forms described herein, dosage forms intended for oral administration are also suitably formulated to provide controlled-, sustained-, and/or delayed release of the active ingredient. Typically, these would include delayed-release oral tablets, capsules and multiparticulates, as well as enteric-coated tablets and capsules which prevent release and adsorption of the active ingredient in the stomach of the patient and facilitate enteric delivery distal to the stomach, i.e., in the intestine. Other typical oral dosage forms would include sustained-release oral tablets, capsules, and multiparticulates which provide systemic delivery of the active ingredient in a controlled manner over a prolonged period of time, e.g., a 24-hour period. Where rapid delivery of the active ingredient is required or desirable, a controlled-release oral dosage form may be prepared in the form of a fast-dissolving tablet, which would also preferably include highly soluble salt forms of the active ingredient.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated herein by reference in their entireties.

What is claimed is:

1. A compound selected from the group consisting of:

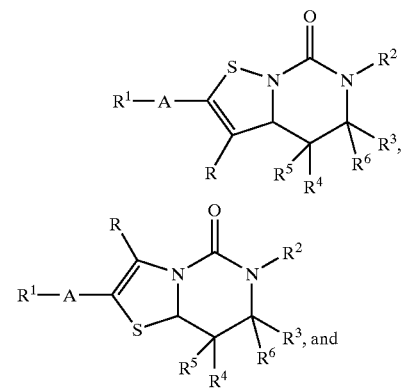

-continued $$R^1-A \overset{N-N}{\underset{S}{\diagup}} \overset{O}{\underset{R^5}{\diagdown}} \overset{R^2}{\underset{R^4}{\diagdown}} R^3, \text{or}$$

a pharmaceutically acceptable salt thereof, wherein A is —NR(C=O), —(C=O)NR, $(C_2-C_6)$ alkynyl-, or a bond;

wherein each R, $R^1$, $R^2$, $R^3$, $R^5$, and $R^6$ are the same or different, where ever they appear, and each is independently selected from the group consisting of $(C_1-C_6)$alkyl-, $(C_2-C_6)$alkenyl-, $(C_2-C_6)$alkynyl-, $(C_3-C_{10})$cycloalkyl-, $(C_6-C_{10})$aryl-, $(C_1-C_{10})$heterocyclyl-, $(C_1-C_{10})$heteroaryl-, $(C_3-C_{10})$cycloalkyl-$(C_1-C_6)$alkyl-, $(C_6-C_{10})$aryl-$(C_1-C_6)$alkyl-, $(C_1-C_{10})$heterocyclyl-$(C_1-C_6)$alkyl-, $(C_1-C_{10})$heteroaryl-$(C_1-C_6)$alkyl-, $(C_3-C_{10})$cycloalkyl-$(C_2-C_6)$alkenyl-, $(C_6-C_{10})$aryl-$(C_2-C_6)$alkenyl-, $(C_1-C_{10})$heterocyclyl-$(C_2-C_6)$alkenyl-, $(C_6-C_{10})$aryl-$(C_2-C_6)$alkenyl-, $(C_1-C_{10})$heteroaryl-$(C_2-C_6)$alkenyl-, $C_3-C_{10}$ cycloalkyl-$(C_2-C_6)$alkynyl-, $(C_6-C_{10})$aryl-$C_2-C_6$ alkynyl-, $C_1-C_{10}$heterocyclyl-$C_2-C_6$alkynyl-, $(C_1-C_{10})$heteroaryl-$(C_2-C_6)$alkynyl-; wherein each of the aforesaid group members, $(C_1-C_6)$alkyl-, $(C_2-C_6)$alkenyl-, $(C_2-C_6)$alkynyl-, $(C_3-C_{10})$cycloalkyl-, $(C_6-C_{10})$aryl-, $(C_1-C_{10})$heterocyclyl-, $C_1-C_{10}$ heteroaryl-, $C_3-C_{10}$cycloalkyl-$C_1-C_6$)alkyl-, $(C_6-C_{10})$aryl-$(C_1-C_6)$alkyl-, $(C_1-C_{10})$heterocyclyl-$(C_1-C_6)$alkyl-, $(C_1-C_{10})$heteroaryl-$(C_1-C_6)$alkyl-, $C_3-C_{10}$cycloalkyl-$(C_2-C_6)$alkenyl-, $(C_6-C_{10})$aryl-$(C_2-C_6)$alkenyl-, $(C_1-C_{10})$heterocyclyl-$(C_2-C_6)$alkenyl-, $(C_6-C_{10})$aryl-$(C_2-C_6)$alkenyl-, $(C_1-C_{10})$heteroaryl-$(C_2-C_6)$alkenyl-, $C_3-C_{10}$cycloalkyl-$(C_2-C_6)$alkynyl-, $(C_6-C_{10})$aryl-$(C_2-C_6)$alkynyl-, $(C_1-C_{10})$heterocyclyl-$(C_2-C_6)$alkynyl-, and $(C_1-C_{10})$heteroaryl-$(C_2-C_6)$alkynyl-, may be optionally independently substituted with one to three suitable substituents selected from the group consisting of hydrogen, halogen, hydroxy, —CN, $(C_1-C_4)$alkyl-, $(C_1-C_4)$alkoxy-, $CF_3$—, $CF_3O$—, $(C_6-C_{10})$aryl-, $(C_1-C_{10})$heteroaryl-, $(C_6-C_{10})$aryl-$(C_1-C_4)$alkyl-, $(C_1-C_{10})$heteroaryl-$(C_1-C_4)$alkyl-, HO(C=O)—, $(C_1-C_4)$alkyl-(O)(C=O)—, $(C_1-C_4$alkyl-(O)(C=O) $(C_1-C_4)$alkyl-, $C_1-C_4$)alkyl-(C=O)—, $(C_1-C_4)$alkyl-(C=O)$(C_1-C_4)$alkyl-, —(S=O)R, —(SO$_2$)R, and NR$^7$R$^8$ wherein R$^7$ and R$^8$ are independently selected from hydrogen, $(C_1-C_6)$alkyl;

R, $R^3$, $R^5$, and $R^6$ may further be hydrogen; and $R^4$ is selected from the group consisting of hydrogen and $(C_1-C_6)$alkyl-, and $R^4$ may be optionally substituted with one to three suitable substituents selected from the group consisting of halogen, hydroxy, —CN, $CF_3$—, and $CF_3O$—.

2. The compound of claim 1, wherein $R^1$ is independently selected from $(C_3-C_{10})$cycloalkyl-$(C_1-C_6)$alkyl-, $(C_6-C_{10})$aryl-$(C_1-C_6)$alkyl-, $(C_1-C_{10})$heterocyclyl-$(C_1-C_6)$alkyl-, $(C_1-C_{10})$heteroaryl-$(C_1-C_6)$alkyl-, $(C_3-C_{10})$cycloalkyl-$(C_2-C_6)$alkenyl-, $(C_6-C_{10})$aryl-$(C_2-C_6)$alkenyl-, $(C_1-C_{10})$heterocyclyl-$(C_2-C_6)$alkenyl-, $(C_1-C_{10})$heteroaryl-$(C_2-C_6)$alkenyl-, $(C_3-C_{10})$cycloalkyl-$C_2-C_6$)alkynyl-, $(C_6-C_{10})$aryl-$(C_2-C_6)$alkynyl-, $(C_1-C_{10})$heterocyclyl-$(C_2-C_6)$alkynyl-, and $(C_1-C_{10})$heteroaryl-$(C_2-C_6)$alkynyl-.

3. The compound of claim 1, wherein $R^2$ is independently selected from $(C_3-C_{10})$cycloalkyl-$(C_1-C_6)$alkyl-, $(C_6-C_{10})$aryl-$(C_1-C_6)$alkyl-, $(C_1-C_{10})$heterocyclyl-$(C_1-C_6)$alkyl-, $(C_1-C_{10})$heteroaryl-$(C_1-C_6)$alkyl-, $(C_3-C_{10})$cycloalkyl-$(C_2-C_6)$alkenyl-, $(C_6-C_{10})$aryl-$C_2-C_6$alkenyl-, $(C_1-C_{10})$heterocyclyl-$(C_2-C_6)$alkenyl-, $(C_1-C_{10})$heteroaryl-$(C_2-C_6)$alkenyl-, $(C_3-C_{10})$cycloalkyl-$(C_2-C_6)$alkynyl-, $(C_6-C_{10})$aryl-$(C_2-C_6)$alkynyl-, $(C_1-C_{10})$heterocyclyl-$(C_2-C_6)$alkynyl-, and $(C_1-C_{10})$heteroaryl-$(C_2-C_6)$alkynyl-.

4. The compound as in claims 1, 2, or 3, wherein $R^1$ and $R^2$ are each independently selected from $(C_3-C_{10})$cycloalkyl-$(C_1-C_6)$alkyl-, $(C_6-C_{10})$aryl-$(C_1-C_6)$alkyl-, $(C_1-C_{10})$heterocyclyl-$(C_1-C_6)$alkyl-, $(C_1-C_{10})$heteroaryl-$(C_1-C_6)$alkyl-, $(C_3-C_{10})$cycloalkyl-$(C_2-C_6)$alkenyl-, $(C_6-C_{10})$aryl-$(C_2-C_6)$alkenyl-, $(C_1-C_{10})$heterocyclyl-$(C_2-C_6)$alkenyl-, $(C_1-C_{10})$heteroaryl-$(C_2-C_6)$alkenyl-, $(C_3-C_{10})$cycloalkyl-$(C_2-C_6)$alkynyl-, $(C_6-C_{10})$aryl-$(C_2-C_6)$alkynyl-, $(C_1-C_{10})$heterocyclyl-$(C_2-C_6)$alkynyl-, and $(C_1-C_{10})$heteroaryl-$(C_2-C_6)$alkynyl-.

5. The compound according to claim 4, wherein $R^1$ and $R^2$ are each independently selected from $(C_6-C_{10})$aryl-$(C_1-C_6)$alkyl- and $(C_1-C_{10})$heteroaryl-$(C_1-C_6)$alkyl-.

6. The compound of claim 5, wherein $R^3$, $R^4$, $R^5$, and $R^6$ are each independently selected from the group consisting of hydrogen and $(C_1-C_6)$alkyl-.

7. A pharmaceutical composition for the treatment of arthritis in a mammal, including a human, comprising an amount of a compound of claim 1, or a pharmaceutically acceptable salt thereof, effective in such treatment and a pharmaceutically acceptable carrier.

8. A method for treating arthritis, comprising administering to a patient suffering from an arthritis disease a nontoxic antiarthritic effective amount of a compound of claim 1, or a pharmaceutically acceptable salt thereof.

9. The method according to claim 8, wherein the arthritis is osteoarthritis or rheumatoid arthritis.

* * * * *